(12) United States Patent
Rieu et al.

(10) Patent No.: US 6,531,469 B1
(45) Date of Patent: Mar. 11, 2003

(54) SUBSTITUTED 1-(4-PIPERIDYL)-3-(ARYL) ISOTHIOUREAS THEIR PREPARATION AND THEIR THERAPEUTIC APPLICATION

(75) Inventors: Jean-Pierre Rieu, Castres (FR); Jean-François Patoiseau, Castres (FR); Gareth John, Castres (FR); Bruno Legrand, Lautrec (FR); Yvan Verscheure, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/889,805

(22) PCT Filed: Jan. 21, 2000

(86) PCT No.: PCT/FR00/00137

§ 371 (c)(1),
(2), (4) Date: Jul. 20, 2001

(87) PCT Pub. No.: WO00/43391

PCT Pub. Date: Jul. 27, 2000

(30) Foreign Application Priority Data

Jan. 22, 1999 (FR) .............................. 99 00706

(51) Int. Cl.[7] .................... C07D 417/12; C07D 413/12; A61K 31/54; A61K 31/535

(52) U.S. Cl. ............... 514/224.2; 514/230.5; 544/50; 544/90

(58) Field of Search .................. 544/50, 90; 514/224.2, 514/230.5

(56) References Cited

FOREIGN PATENT DOCUMENTS

WO   WO 97/05134   *  2/1997

OTHER PUBLICATIONS

Damasio et al., Alzheimer's Disease and related Dementias, Cecil Textbook of Medicine, 20th Edition, vol. 2, pp. 1992–1996.*

Layzer et al., Degenerative Diseases of the Nervous System, Cecil Textbook of Medicine, 20th Edition, vol. 20, pp. 2050–2057, 1996, 1996.*

* cited by examiner

Primary Examiner—Deepak Rao
(74) Attorney, Agent, or Firm—The Firm of Hueschen and Sage; G. Patrick Sage

(57) ABSTRACT

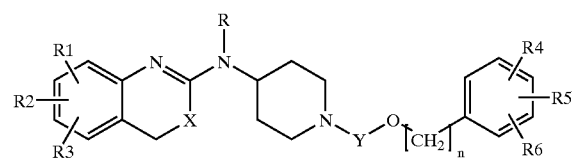

(I)

The invention concerns novel substituted N-benzo(thia/oxa)zines-2-yl-1-arylalkyloxyalkyl-4-piperidinamine, their preparation and their therapeutic use. The invention concerns compounds of formula (1) wherein: X represents an oxygen or sulphur atom; Y represents either an alkylene radical, branched or not and containing 2 to 6 carbon atoms or a $CH_2$—CH(OH)—$CH_2$— radical. R represents a hydrogen, an alkyl radical, branched or not and containing 1 to 7 carbon atoms; $R_1$ to $R_6$, identical or different, represent a hydrogen, a saturated or unsaturated alkyl, branched or not and containing 1 to 5 carbon atoms, a saturated or unsaturated alkyloxy, branched or not and containing 1 to 5 carbon atoms, a halogeno, nitro, hydroxy, acyl or acyloxy group comprising 2 to 3 carbon atoms, an alkylamino group containing 1 to 5 carbon atoms, a trifluoro methyl or trifluoro methoxyl group; n is an integer ranging from 1 to 6 inclusively, and their pure, enantiomers or their mixtures, the therapeutically acceptable mineral and organic salts of the compounds of formula (1) and their possible hydrates.

8 Claims, No Drawings

SUBSTITUTED 1-(4-PIPERIDYL)-3-(ARYL) ISOTHIOUREAS THEIR PREPARATION AND THEIR THERAPEUTIC APPLICATION

The invention relates to novel substituted N-benzo(thia/oxa)zine-2-yl-1-arylalkyloxyalkyl-4-piperidinamines of formula I:

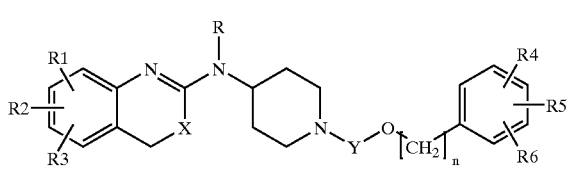

(in which the radicals are as defined in the invention), to their preparation and to their therapeutic application.

In a recent patent from the Applicant (WO 97/05134), N-alkyl-N-[1-(ω-aryloxyalkyl)-4-piperid]-4H-3,1-benzothiazin-2-amines of therapeutic value, particularly in the treatment of myocardial ischemia, were mentioned.

In the course of the structure/activity study, it was decided to increase the space between the phenyl radical and the oxygen via the introduction of an alkylene radical to measure the impact on the cytoprotective activity of such a structural modification. The substitution of the piperidine nitrogen with an arylalkyloxyalkyl radical instead of an aryloxyalkyl radical allowed the identification of a new class of compounds which showed activity superior to that of the compounds of the base series. The compounds of this novel series form the subject of the present invention.

MOLECULES CLAIMED

The molecules of the present invention belong to the class of substituted N-alkyl-N-[1-(ω-(arylalkyloxy)alkyl]-4-piperidyl]-4H-3,1-benzo[thia/oxa)zine-2-amines and are of formula I:

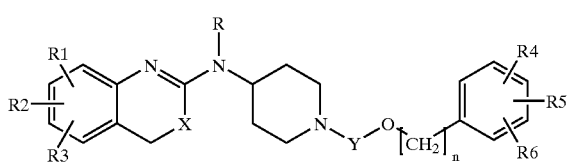

in which:
X represents an oxygen or sulfur atom
Y represents either
  a branched or unbranched alkylene radical containing from 2 to 6 carbon atoms or
  a —$CH_2$—CH(OH)—$CH_2$— radical
R represents a hydrogen, a saturated or unsaturated, branched or unbranched alkyl radical containing from 1 to 7 carbon atoms,
$R_1$ to $R_6$, which may be identical or different, represent:
  a hydrogen,
  a branched or unbranched, saturated or unsaturated alkyl containing from 1 to 5 carbon atoms,
  a branched or unbranched, saturated or unsaturated alkyloxy containing from 1 to 5 carbon atoms,
  a halo group,
  a nitro group,
  a hydroxyl group,
  an acyl or acyloxy group containing from 2 to 3 carbon atoms,
  a dialkylamino group containing from 1 to 5 carbon atoms,
  a trifluoromethyl or trifluoromethoxy group,
n is an integer which may range from 1 to 6 inclusive.

The present invention also includes the therapeutically acceptable mineral or organic salts of the compounds of formula I and the possible hydrates thereof. The invention also relates to processes for preparing the derivatives claimed, and also to their application as medicinal products. The molecules of the present invention of formula I have noteworthy cytoprotective properties, the activity of which is superior to that of the base family claimed in patent WO 97/05134.

SYNTHESIS OF THE COMPOUNDS OF FORMULA I

The compounds of formula I may be prepared according to two main routes, ending either with N-alkylation or with heterocyclization.

1) Synthesis via Final N-alkylation a) When Y represents an alkylene, the compounds of formula I are generally prepared by condensing an arylalkyloxyalkyl halide or mesylate of formula III with an N-(4-piperidyl)-4H-3,1-benzothiazin-2-amine II in the presence of an organic or mineral base in an organic solvent according to the reaction:

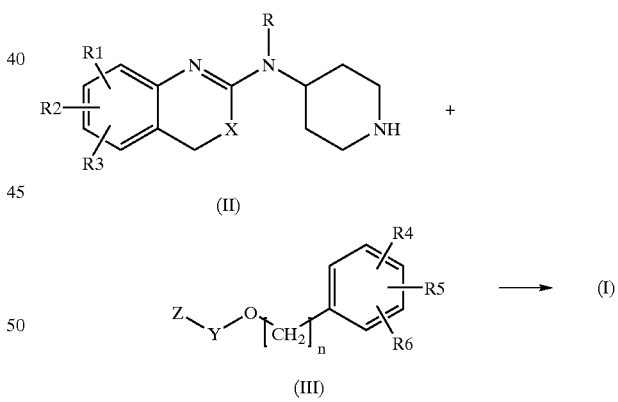

in which Z=Cl, Br, I, or $MeSO_3$.

The method for preparing ethers III varies according to the length of the carbon chain in the divalent alkylene group Y.

When the base chain Y contains more than 3 carbon atoms, the ether is prepared by condensing an excess of the 1,ω-dibromoalkane V with the corresponding alcohol IV in a strong basic medium using a phase-transfer catalyst such as tetrabutylammonium bisulfate according to A. W. Burgstahler et al. (*J. Org. Chem.*, 1977, 42, 566–8) according to the reaction:

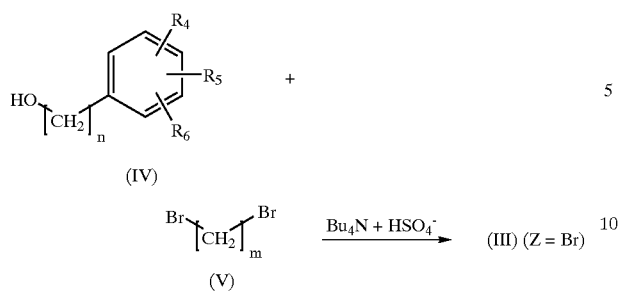

When Y represents a trimethylene, the preceding reaction applied to 1,3-dibromopropane gives the expected derivative III in a low yield (10 to 30%) and allylic ether is above all formed. In this case, it is preferred to use 1-bromo-3-chloropropane to prepare the chloro derivative III (Z=Cl) in a yield of about 50 to 60%.

When Y represents an ethylene, the preceding reaction cannot be performed, and it is preferable to condense the starting alcohol IV with ethylene carbonate in the presence of sodium hydride according to Van den Brock L. A. G., Vermaas D. J. et al. (*Recueil Trav. Chim. Pay-Bas*, 1994, 113, 507–516). In this case, an intermediate (2-arylalkoxy) ethanol VI is obtained, which may be activated in the form of mesylate III (Z=MeSO$_3$—) after treatment with mesyl chloride according to the reaction:

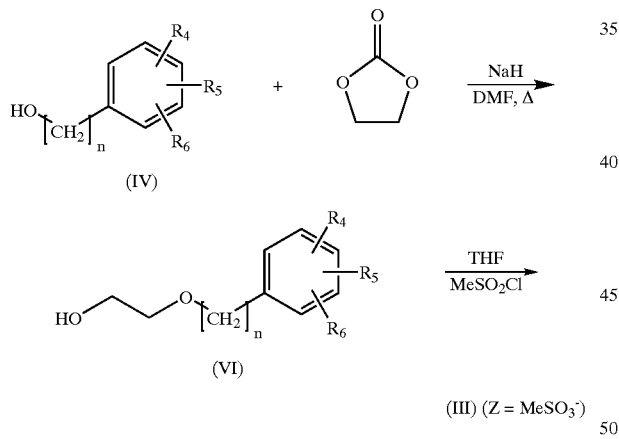

b) When Y represents a —CH$_2$—CH(OH)—CH$_2$— radical, the compounds I of the present invention are similarly prepared, but using an arylalkyloxymethoxy epoxide VII as alkylating agent, according to the reaction:

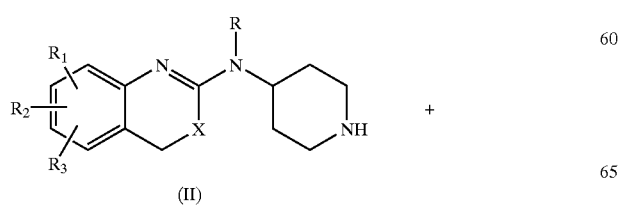

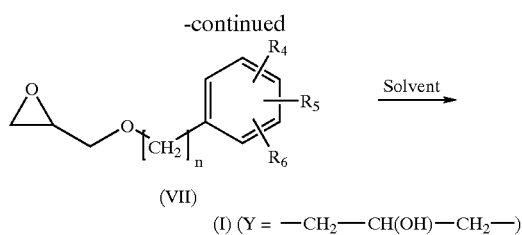

The glycidyl ethers VII are prepared by condensing epichlorohydrin with the corresponding alcohols IV by phase transfer catalysis by means of the process already described (Mouzin G. et al. *Synthesis*, 1983, 117–119) according to the reaction:

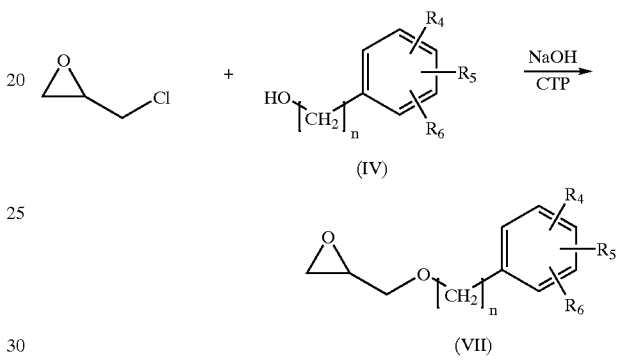

When the starting alcohols IV are not commercially available, they are obtained from the corresponding ethyl or methyl esters VIII by reduction in the presence of aluminohydride:

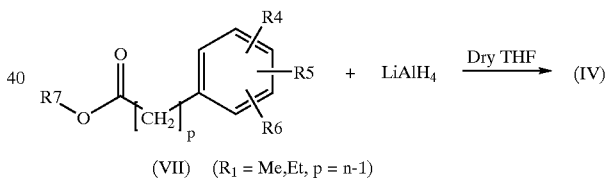

The synthesis of the heterocycle III has already been described in the application of the base series WO 97/05314.

2) Preparation by Final Heterocyclization

The compounds I may be prepared by final cyclization using two types of activation of the amines attached to the heterocycle.

a) In a first case, the aromatic amine may be activated in the form of o-bromomethyl phenyl isothiocyanate IX as described in patent WO 97/05314, by reaction with the suitably substituted aminopiperidine X according to:

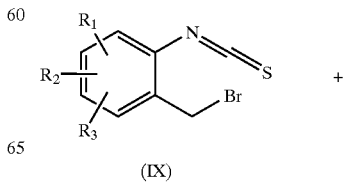

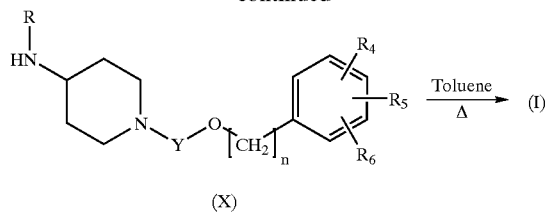

b) The activation may also derive from the amine borne by the piperidine nucleus. The activation may be produced in two ways depending on the nature of the radical R and always takes places in two steps:

If R is hydrogen, the amine X may be activated in the form of iso(thio)cyanate XI by reaction with triphosgene or (thio)carbonyl diimidazole according to Staab H. A. and G. Walther (*Ann.*, 1962, 657, 104–107), for example:

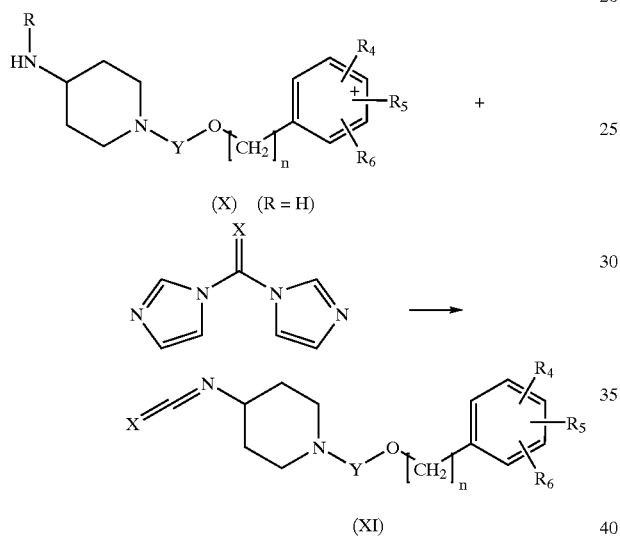

This compound reacts readily with a suitably substituted ortho-aminobenzyl alcohol XII to give a hydroxy(thio)urea XIII (R=H) which is readily cyclized in aqueous strong acid medium to the compound of formula I which is the subject of the present invention, as described in patent application WO 97/05314:

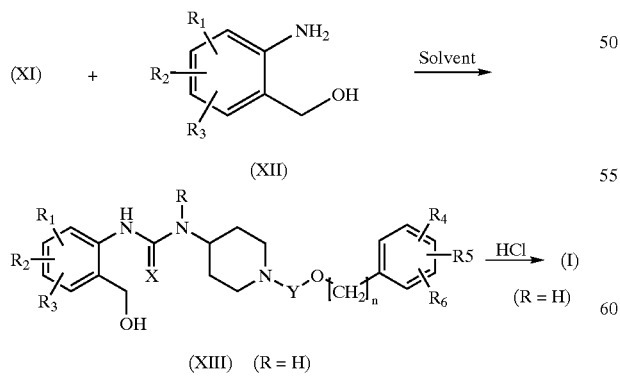

By N-alkylation of I (R=H) with an alkyl halide after sodation with NaH, the compound I in which R=alkyl is similarly prepared.

When R is other than a hydrogen, the activation of the amine X is carried out with thiophosgene or triphosgene to give a (thio)carbamoyl chloride XTV in an aprotic solvent in basic medium.

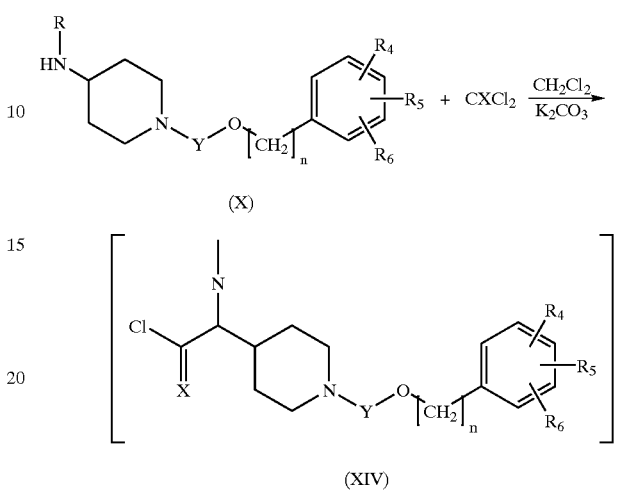

This derivative is not isolated, but is added directly to the o-aminobenzyl alcohol XII to give the corresponding hydroxy(thio)urea XIII which is cyclized by the same process as above:

When they are not commercially available, the aminobenzyl alcohols XII are prepared by reducing the suitably substituted corresponding anthranilic esters.

The aminopiperidines X are prepared by adapting the process described in the base patent WO 97/05314 by N-alkylation of the protected 4-piperidones XV with the corresponding halo ethers III, followed by a deprotection of the compound obtained, to give the keto amine XVI which undergoes a reductive amination with the amine R—NH$_2$ (XVII) in the presence of borane-pyridine or sodium borohydride triacetate according to the scheme:

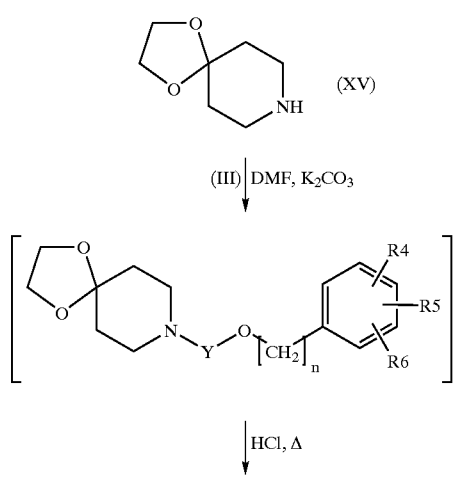

-continued

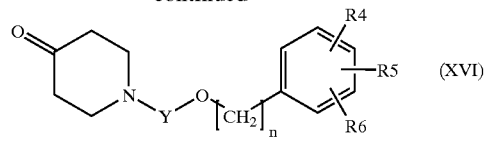

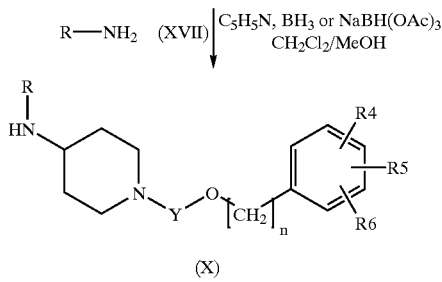

EXAMPLE 1

N-Methyl-N-[1-[5-(4-fluorobenzyloxy)pentyl]-4-piperidyl]-4H-3,1-benzothiazin-2-amine Hydrogen Fumarate (1)

1.1) 1-[5-Bromopentyloxymethyl]-4-fluorobenzene (1.1). A mixture containing 2 g (15.8 mmol) of 4-fluorobenzyl alcohol, 18.3 g (79 mmol) of 1,5-dibromopentane, 3.2 g (79 mmol) of sodium hydroxide pellets in 6.4 ml of water and 270 mg (0.79 mmol) of tetrabutylammonium bisulfate is stirred vigorously for 2 days at 25° C. The reaction mixture is extracted with ether, washed with water and with brine and then dried over anhydrous sodium sulfate. After removal of the mineral salt, the mixture is evaporated to dryness under vacuum and the residual oil is rectified under vacuum. 5.12 g (yield: 63%) of a colorless oil of formula 1.1 are recovered:

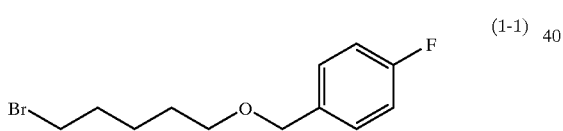

(1-1)

Empirical formula: $C_{12}H_{16}BrFO$; Molar mass: 275.168; Colorless oil; Boiling point: 97–102° C./0.1 mbar; NMR (CDCl$_3$) δ: 1.15–1.73 (m, 4H); 1.75–1.95 (m, 2H); 3.28–3.56 (m, 4H); 4.44 (s, 2H); 6.9–7.1 (m, 2H); 7.2–7.37 (m, 2H)

1.2) N-Methyl-N-[1-[5-(4-fluorobenzyloxy)pentyl]-4-piperidyl]-4H-3,1-benzothiazin-2-amine hydrogen fumarate (1). A solution of 600 mg (2.3 mmol) of N-methyl-N-(4-piperidyl)-4H-3,1-benzothiazin-2-amine (prepared according to patent WO 97/05134) and 633 mg (2.3 mmol) of 1-[5-bromopentyloxymethyl]-4-fluoro-benzene in 10 ml of DMF is treated with 480 mg (3.5 mmol) of dry, ground K$_2$CO$_3$ and a small amount of potassium iodide, and then heated for 3 h at 90° C. with stirring. After cooling to 30–40° C., the mixture is evaporated to dryness under vacuum and the residue is partitioned in a CH$_2$Cl$_2$/water mixture. The phases are separated. The organic phase is washed with water and with brine and then dried over anhydrous sodium sulfate. The residue obtained after removing the minerals and evaporating the filtrate is purified by flash chromatography, eluting with a 95/4.5/0.5 CH$_2$Cl$_2$/CH$_3$OH/NH$_4$OH mixture. The fractions containing the expected compound are combined and evaporated to dryness to give 710 mg of base which is taken up in ethanol and treated with one equivalent of fumaric acid dissolved in 2 ml of hot ethanol. The mixture is allowed to cool slowly to 25° C. and the crystals (m=740 mg, yield: 56%) of salt of formula 1 are then filtered off:

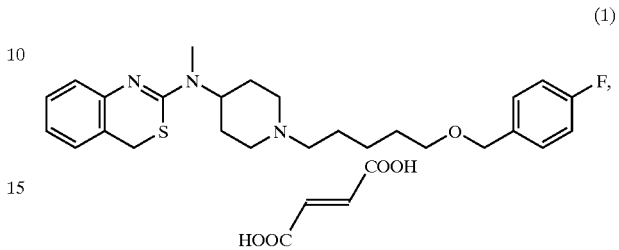

(1)

Empirical formula: $C_{30}H_{38}FN_3O_5S$; Molar mass: 571.71; White crystals; Melting point: 167° C.; NMR (DMSO d$_6$) δ: 1.2–1.75 (m, 8H); 1.8–2.1 (m, 2H); 2.25–2.65 (m, 4H); 3 (s, 3H); 3.1–3.3 (m, 2H); 3.41 (t, 2H); 3.94 (s, 2H); 4.25–4.6 (m, 1H); 4.41 (s, 2H); 6.55 (s, 2H); 6.93 (t, 2H); 7.06–7.23 (m, 4H); 7.26–7.42 (m, 2H); 10–12 (m, 2H).

EXAMPLE 2

N-Methyl-N-[1-[4-(4-fluorobenzyloxy)butyl]-4-piperidyl]-4H-3,1-benzothiazin-2-amine Hydrogen Fumarate (2)

2.1) 1-[4-Bromobutyloxymethyl]-4-fluorobenzene (2.1). By applying the procedure of Example 1.1 to 10.3 g of 1,4-dibromobutane, the compound of formula 2.1 is prepared in a yield of 61%:

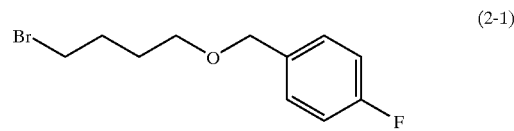

(2-1)

Empirical formula: $C_{11}H_{14}BrFO$; Molar mass: 261.13; Colorless oil. Boiling point: 123–125° C./0.46 mbar; NMR (CDCl$_3$) δ: 1.6–1.82 (m, 2H); 1.85–2.1 (m, 2H); 3.32–3.58 (m, 2H); 4.44 (s, 2H); 6.92–7.08 (m, 2H); 7.22–7.35 (m, 2H).

2.2) N-Methyl-N-[1-[4-(4-fluorobenzyloxy)butyl]-4-piperidyl]-4H-3,1-benzothiazin-2-amine hydrogen fumarate (2). The condensation of 660 mg (2.53 mmol) of the bromo compound 2.1 above with 600 mg (2.3 mmol) of N-methyl-N-(4-piperidyl)-4H-3,1-benzothiazin-2-amine gives 792 mg (yield: 62%) of white crystals of formula 2.

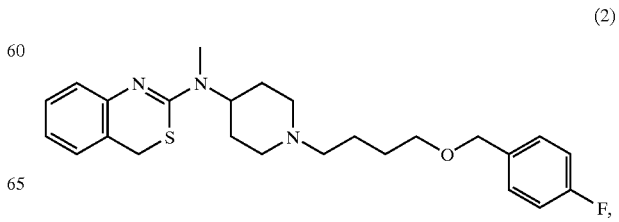

(2)

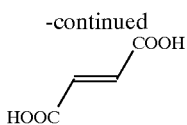

Empirical formula: $C_{29}H_{36}FN_3O_5S$; Molar mass: 557.67; White crystals; Boiling point: 174–175° C.; NMR (CDCl$_3$) δ: 1.4–1.7 (m, 6H); 1.76–2.1 (m, 2H); 2.32 (t, 2H); 2.42–2.64; (m, 2H); 2.99 (s, 3H); 3.06–3.15 (m, 2H); 3.41 (t, 2H); 3.91 (s, 2H); 4.25–4.6 (m, 1H); 4.4 (s, 2H); 6.55 (s, 2H); 6.91 (t, 2H); 7.07–7.25 (m, 4H); 7.25–7.4 (m, 2H); 10.5–12.5 (m, 2H).

EXAMPLE 3

N-Methyl-N-[1-[3-(4-fluorobenzyloxy)propyl]-4-piperidyl]-4H-3,1-benzothiazin-2-amine Hydrogen Fumarate (3)

3.1) 1-(3-Bromopropyloxymethyl)-4-fluorobenzene (3.1). The condensation of 16 g of 1,3-dibromopropane with 2 g (15.8 mmol) of 4-fluorobenzyl alcohol according to the process of Example 1.1 gives, after distillation, 1.05 g (yield: 27%) of a colorless oil of formula 3.1:

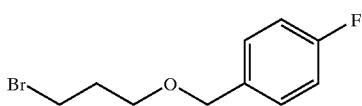

(3-1)

Empirical formula: $C_{10}H_{12}BrFO$; Molar mass: 247.11; Colorless oil; Boiling point: 92–95° C. (0.63 mbar); NMR (CDCl$_3$) δ: 2.05–2.25 (m, 2H); 3.45–3.70 (m, 4H); 4.48 (s, 2H); 6.95–7.12 (m, 2H); 7.22–7.4 (m, 2H). 3.2) N-Methyl-N-[1-[3-(4-fluorobenzyloxy)propyl]-4-piperidyl]-4H-3,1-benzothiazin-2-amine hydrogen fumarate (3). The N-alkylation of 586 mg (2.24 mmol) of N-methyl-N-(4-piperidyl)-4H-3,1-benzothiazin-2-amine with 582 mg (2.35 mmol) of the above bromo derivative 3.1 according to Example 1.2 gives 785 mg (yield: 64%) of compound of formula 3:

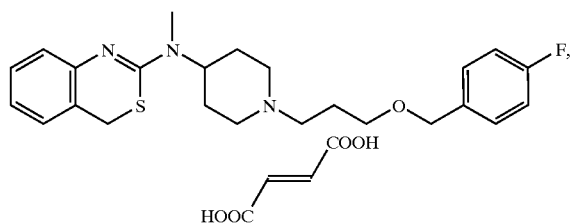

(3)

Empirical formula: $C_{28}H_{34}FN_3O_5S$; Molecular mass: 543.64; White crystals; Melting point: 163–164° C.; NMR (DMSO d$_6$) δ: 1.57–2.1 (m, 6H); 2.34 (t, 2H); 2.55–2.7 (m, 2H); 3.02 (s, 3H); 3.08–3.2 (m, 2H); 3.48; (t, 2H); 3.96 (s, 2H); 4.25–4.57 (m, 1H); 4.45 (s, 2H); 6.6 (s, 2H); 6.95 (t, 2H); 7.05–7.28 (m, 4H); 7.3–7.5 (m, 2H); 11–13 (m, 2H).

EXAMPLE 4

N-Methyl-N-[1-[2-(4-fluorobenzyloxy)ethyl]-4-piperidyl]-4H-3,1-benzothiazin-2-amine Hydrogen Fumarate (4)

4.1) 4-Fluoro-1-[2-hydroxyethoxymethyl]benzene (4.1). A solution of 4 g (31.7 mmol) of 4-fluorobenzyl alcohol in 30 ml of dry DMF is cooled to 0° C. and then treated over 25 min with 3.8 g (95 mmol) of 60% sodium hydride. Stirring is then continued for 100 min a t 25° C., followed by dropwise addition of 3.6 g (63.4 mmol) of ethylene carbonate dissolved in 20 ml of DMF, and the mixture is stirred for 1 h at 25° C. The reaction mixture is poured onto crushed ice, extracted with ether, washed with water and brine, and dried over anhydrous sodium sulfate. The mineral salt is filtered off and the filtrate is evaporated to dryness, and the residual oil is then purified by flash chromatography, eluting with a 90/10 and then 70/30 petroleum ether/ethyl acetate mixture. The fractions containing the expected ether are recovered in the usual way to give 5.95 g (yield: 56%) of the hydroxy ether of formula 4.1:

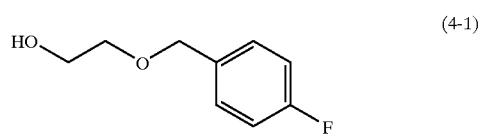

(4-1)

Empirical formula: $C_9H_{11}FO_2$; Molar mass: 170.18; Pale yellow oil; NMR (CDCl$_3$) δ: 2.1 (m, 1H); 3.52–3.63 (m, 2H); 3.75 (t, 2H); 4.51 (s, 2H); 6.95–7.12 (m, 2H); 7.14–7.45 (m, 2H).

4.2) 2-[4-Fluorobenzyloxy]ethyl mesylate (4.2). A solution of 1.5 g (8.8 mmol) of the above alcohol 4.1 in 15 ml of dry DHF is cooled to 0° C. and then treated with 1.84 ml (1.34 g; 13.2 mmol) of triethylamine and dropwise with 1.11 g (9.7 mmol) of mesyl chloride. The mixture is allowed to return to 25° C. and is maintained at this temperature for a further ½ h, the mixture is then filtered, 20 ml of water are added to the filtrate and the resulting mixture is extracted with ether and then washed with water and with brine, and dried over sodium sulfate. The mesylate is recovered after evaporation to dryness (m=2.29 g, yield: 92%) and is of formula 4.2:

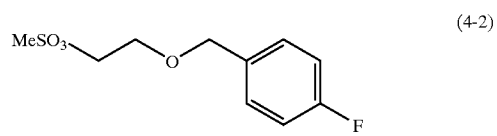

(4-2)

Empirical formula: $C_{10}H_{13}FO_4S$; Molar mass: 248.26; Yellow oil; NMR (CDCl$_3$) δ: 3.03 (s, 3H); 3.65–3.8 (m, 2H); 4.35–4.45; (m, 2H); 4.54-(s, 2H); 6.95–7.12 (m, 2H); 7.22–7.38 (m, 2H).

4.3) N-Methyl-N-[1-[2-(4-fluorobenzyloxy)ethyl]-4-piperidyl]-4H-3,1-benzothiazin-2-amine hydrogen fumarate (4). Using 2-[4-fluorobenzyloxy]ethyl mesylate (627 mg or 2.53 mmol) and applying the process of Example 1.2, 920 mg (yield: 76%) of a white powder of formula 4 are prepared:

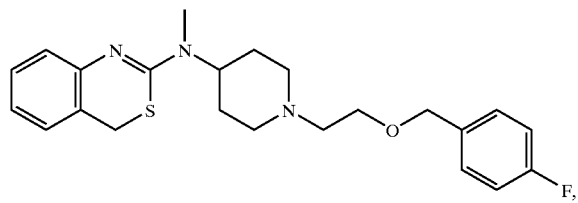

(4)

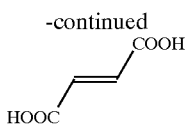

Empirical formula: $C_{27}H_{32}FN_3O_5S$; Molar mass: 529.61; White crystals; Melting point: 160–161° C.; NMR (DMSO $d_6$) δ: 1.45–2.05 (m, 4H); 2.33 (t, 2H); 2.71; (t, 2H); 3.01 (s, 3H); 3–3.15 (m, 2H); 3.59 (t, 2H); 3.93 (s, 2H); 4.25–4.52 (m, 1H); 4.47 (s, 2H); 6.59 (s, 2H); 6.93 (t, 2H); 7.05–7.28 (m, 4H); 7.3–7.46 (m, 2H); 11-3 (m, 2H).

EXAMPLE 5

N-Methyl-N-[1-[4-[2-(4-fluorophenyl)ethoxy]butyl]-4-piperidyl]-4H-3,1-benzothiazin-2-amine Hydrogen Fumarate (5)

5.1) 4-Fluoro-1-[2-[4-bromobutyloxy]ethyl]benzene (5.1). The O-alkylation of 2 g (14.3 mmol) of 4-fluorophenethyl alcohol with 15.4 g (71.3 mmol) of 1,4-dibromobutane according to 1.1 gives 3.1 g (yield: 79%) of compound of formula 5.1:

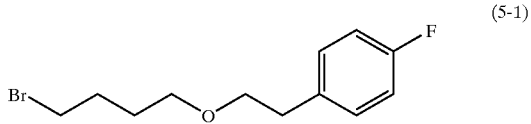

Empirical formula: $C_{12}H_{16}BrFO$; Molar mass: 275.16; Colorless oil; Boiling point: 115–120° C./0.24 mbar; NMR (CDCl$_3$) δ: 1.6–1.8 (m, 2H); 1.8–2.05 (m, 2H); 2.85; (t, 2H); 3.3–3.5 (m, 4H); 3.6 (t, 2H); 6.9–7.05 (m, 2H); 7.07–7.26 (m, 2H).

5.2) N-Methyl-N-[1-[4-[2-(4-fluorophenyl)ethoxy]butyl]-4-piperidyl]-4H-3,1-benzothiazin-2-amine hydrogen fumarate (5). The application of process 1.2 to 665 mg (2.41 mmol) of bromo derivative 5.1 above gives 780 mg (yield: 59%) of salt of formula 5:

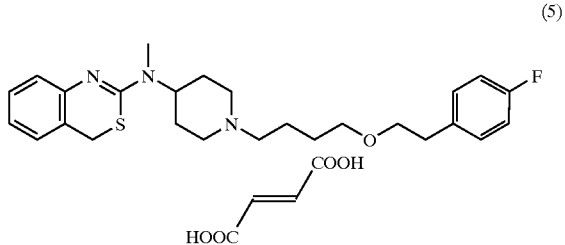

Empirical formula: $C_{30}H_{38}FN_3O_5S$; Molar mass: 571.69; White crystals; Melting point: 173–174° C.; NMR (DMSO $d_6$) δ: 1.35–2.1 (m, 8H); 2.29 (t, 2H); 2.42–2.57 (m, 2H); 2.78 (t, 2H); 3 (s, 3H); 3–3.2 (m, 2H); 3.37 (t, 2H); 3.53 (t,2H); 3.93 (s, 2H); 4.39 (m, 1H); 6.56 (s, 2H); 6.92 (t, 2H); 7–7.32 (m, 6H); 11.5–13 (m, 2H).

EXAMPLE 6

N-Methyl-N-[1-[3-[2-(4-fluorophenyl)ethoxy] propyl]-4-piperidyl]-4H-3,1-benzothiazin-2-amine Hydrogen Fumarate (6)

6.1) 4-Fluoro-1-[2-(3-chloropropoxy)ethyl]benzene 6.1. A solution of 86 g (2.14 mol) of NaOH pellets in 86 g of water is stirred and then cooled to 25° C., after which it is treated with 20 g (0.143 mol) of 4-fluorophenethyl alcohol, with 113 ml (1.14 mol) of 1-bromo-3-chloropropane and then with 4.85 g (14 mmol) of tetrabutylammonium bisulfate. Vigorous stirring is maintained for 4 h at 25° C. and the mixture is then extracted with ether, washed with water and brine, and dried over anhydrous sodium sulfate. After removing the mineral salt, the filtrate is evaporated to dryness and the residual oil is rectified under vacuum to give 20.3 g (yield: 65%) of product of formula 6.1:

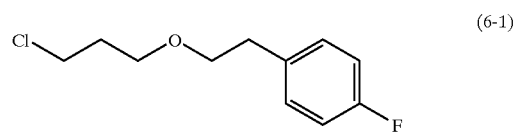

Empirical formula: $C_{11}H_{14}ClFO$; Molar mass: 216.67; Colorless oil; Boiling point: 94–97° C./0.4 mbar; NMR (ClCl$_3$ $d_6$) δ: 2.08 (q, 2H); 2.85 (t, 2H); 3.46 (t, 2H); 3.55 (t, 2H); 3.63 (t, 2H); 6.97 (t, 2H); 7.1–7.2 (m, 2H).

6.2) N-Methyl-N-[1-[3-[2-(4-fluorophenyl)ethoxy]-propyl]-4-piperidyl]-4H-3,1-benzothiazin-2-amine hydrogen fumarate (6). A solution of 1.48 g (6.83 mmol) of the above compound 6.1 and 1.7 g (6.5 mmol) of N-methyl-N-[4-piperidyl]-4H-3,1-benzothiazin-2-amine in 18 ml of DMF is treated with 945 mg (6.83 mmol) of ground $K_2CO_3$ and 20 mg of KI, and is then maintained on an oil bath at 80° C. for 4 h. After cooling to 25° C., the mixture is treated as in Example 1.2 to give, after purification by flash chromatography, 3.12 g of crude base, which is salified in the usual manner to give the compound of formula 6.2 (yield: 68%).

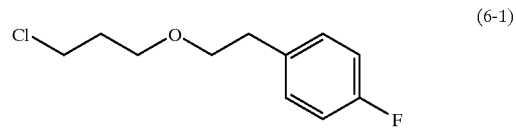

Empirical formula: $C_{29}H_{36}FN_3O_5S$; Molar mass: 557.67; White crystals; Melting point: 163–4° C.; NMR (DMSO $d_6$) δ: 1.6–1.72 (m, 4H); 1.75–1.95 (m, 2H); 2.24 (t, 2H); 2.4–2.58 (m, 2H); 2.79 (t, 2H); 3.02 (s, 3H); 3–3.14 (m, 2H); 3.41 (t, 2H); 3.55 (t, 2H); 3.94 (s, 2H); 4.37 (m, 1H); 6.58 (s, 2H); 6.85–6.98 (m, 2H); 7.02–7.2 (m, 4H); 7.25–7.3 (m, 2H); 10–12 (m, 2H).

EXAMPLE 7

N-Methyl-N-[1-[3-[2-(4-fluorophenyl)ethoxy] propyl]-4-piperidyl]-4H-3,1-benzothiazin-2-amine Dihydrochloride (7)

A solution of 425 mg of base obtained in Example 6.2 in 4 ml of dry ethanol is cooled on an ice bath and then treated dropwise with 0.9 ml of a 2.3N solution of hydrogen chloride in ethanol. After stirring for 10 minutes, 3 to 4 volumes of ethyl ether are added while scratching with a glass rod. The mixture is left overnight in a refrigerator and the crystals of the salt formed are then filtered off, rinsed with ether and then dried in a vacuum jar in the presence of actigel: m=512 mg (yield: 63%) of crystals of formula 7:

(7)

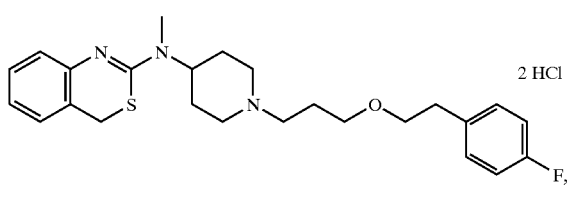

2 HCl

Empirical formula: $C_{22}H_{34}Cl_2FN_3OS$; Molar mass: 514.52; Hygroscopic white crystals (containing 3.2% $H_2O$); Decomposition temperature>110° C.; NMR (DMSO $d_6$) 1.88–2.08 (m, 4H); 2.4–2.53 (m, 2H); 2.81; (t, 2H); 3–3.23 (m, 4H); 3.27 (s, 3H); 3.47 (t, 2H); 3.5–3.65 (m, 4H); 4.3 (s, 2H); 4.57 (m, 1H); 7.11 (t, 2H); 7.2–7.45 (m, 6H); 7.54 (m, 1H); 11.16 (m, 1H).

EXAMPLE 8

N-Methyl-N-[1-[3-[3-(4-fluorophenyl)propoxy] propyl]-4-piperidyl]-4H-3,1-benzothiazin-2-amine Hydrogen Fumarate (8)

8.1) 1-[3-(3-Bromopropoxy)propyl]-4-fluorobenzene (8.1). The etherification reaction carried out according to protocol 1.1 starting with 2 g (13 mmol) of 3-(4-fluorophenyl)propyl alcohol in the presence of 13 g of 1,3-dibromopropane gives, after purification by flash chromatography, 1.05 g (yield: 29%) of compound of formula 8.1:

(8-1)

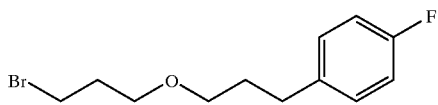

Empirical formula: $C_{12}H_{16}BrFO$; Molar mass: 275.17; Amber-colored oil; NMR (CDCl$_3$) δ: 1.75–1.95 (m, 2H); 2–2.18 (m, 2H); 2.64; (t, 2H); 3.4 (t, 2H); 3.51 (t, 4H); 6.95 (t, 2H); 7.05–7.2 (m, 2H).

8.2) N-Methyl-N-[1-[3-[3-(4-fluorophenyl)propoxy]-propyl]-4-piperidyl]-4H-3,1-benzothiazin-2-amine (8.2). Using the process of example 1.1, but starting with 600 mg (2.3 mmol) of the above bromo derivative 8.1, 995 mg (yield 75%) of compound of formula 8 are prepared:

(8)

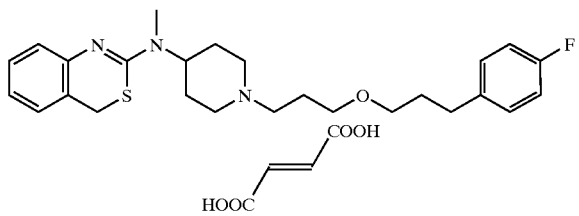

Empirical formula: $C_{30}H_{38}FN_3O_5S$; Molar mass: 571.71; White crystals; Melting point: 176° C.; NMR (DMSO $d_6$) δ: 1.57–2.07 (m, 8H); 2.34 (t, 2H); 2.52–2.66 (m, 4H); 3.01 (s, 3H); 3.05–3.22 (m, 3H); 3.25–3.45 (m, 4H); 3.94 (s, 2H); 4.04 (m, 1H); 6.57 (s, 2H); 6.93 (t, 2H); 7–7.3 (m, 6H); 10–12 (m, 1H).

EXAMPLE 9

N-Methyl-N-l1-[2-[2-(4-fluorophenyl)ethoxy]ethyl]-4-piperidyl] -4H-3,1-benzothiazin-2-amine Hydrogen Fumarate (9)

9.1) 4-Fluoro-1-[2-[2-hydroxyethoxy]ethyl]benzene (9.1). Starting with 4 g (28.5 mmol) of 4-fluorophenethyl alcohol and 5.03 g (57 mmol) of ethylene carbonate according to protocol 4.1, 2.1 g (yield: 40%) of the hydroxy ether of formula 9.1 are prepared:

(9-1)

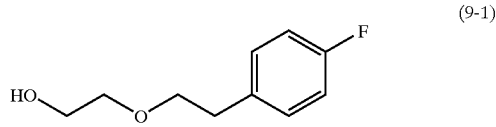

Empirical formula: $C_{10}H_{13}FO_2$; Molar mass: 184.20; Pale yellow oil; NMR (CDCl$_3$) δ: 1.82 (s, 1H); 2.86 (t, 2H); 3.5–3.8 (m, 6H); 6.9–7.05 (m, 2H); 7.12–7.24 (m, 2H).

9.2) 2-[2-(4-Fluorophenyl)ethoxy]ethyl mesylate (9.2). 900 mg of the above alcohol 9.1 are treated in the presence of 616 mg (5.4 mmol) of mesyl chloride according to 4.2, to give 1.17 g (yield: 91%) of a yellow oil of formula 9.2:

(9-2)

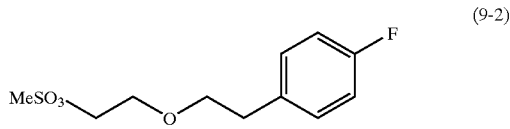

Empirical formula: $C_{11}H_{15}FO_4S$; Molar mass: 262.29; Yellow oil; NMR (CDCl$_3$) δ: 2.83 (t, 2H); 2.92 (s, 3H); 3.55–3.7 (m, 4H); 4.26–4.37 (m, 2H); 6.9–7.04 (m, 2H); 7.08–7.23 (m, 2H).

9.3) N-Methyl-N-[1-[2-[2-(4-fluorophenyl)ethoxy]ethyl]-4-piperidyl]-4H-3,1-benzothiazin-2-amine (9). Working according to the process of Example 1.2, starting with 773 mg (2.95 mmol) of mesylate 9.2 above, 920 mg (yield: 63%) of compound of formula 9 are obtained:

(9)

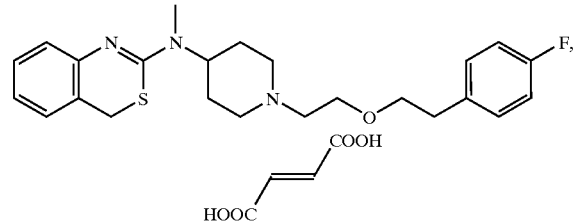

Empirical formula: $C_{28}H_{34}FN_3O_5S$; Molar mass: 543.64; Pulverulent white crystals; Melting point: 145–6° C.; NMR (DMSO $d_6$) δ: 1.52–1.68 (m, 2H); 1.72–1.9 (m, 2H); 2.23 (t, 2H); 2.61 (s, 2H); 2.8 (t, 2H); 2.95–3.1 (m, 5H); 3.5–3.63 (m, 4H); 3.94 (s, 2H); 4.32 (m, 1H); 6.6 (s, 2H); 6.88–6.97 (m, 2H); 7.05–7.21 (m, 4H); 7.25–7.32 (m, 2H); 11–13 (m, 2H).

EXAMPLE 10

N-Methyl-N-[1-[5-(3,4-difluorophenylmethoxy) pentyl]-4-piperidyl]-4H-3,1-benzothiazin-2-amine Hydrogen Fumarate (10)

10.1) 1-(5-Bromopentyloxymethyl)-3,4-difluorobenzene (10.1) The etherification of 2 g (13.9 mmol) of 3,4- difluorobenzyl alcohol in the presence of 16 g of 1,5-dibromopentane, according to the process described in Example 1.1 gives 2.96 g (yield: 72%) of compound of formula 10.1:

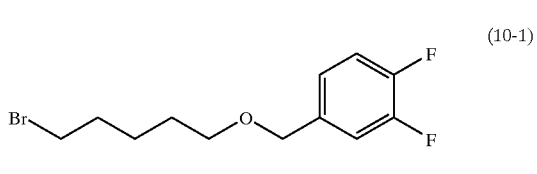
(10-1)

Empirical formula: $C_{12}H_{15}BrF_2O$; Molar mass: 293.16; Colorless oil; Boiling point: 110–120° C./0.1 mbar NMR (CDCl$_3$) δ: 1.4–1.74 (m, 4H); 1.77–1.98 (m, 2H); 3.33–3.56 (m, 4H); 4.44 (s, 2H); 6.95–7.24 (n, 3H). 10.2) N-Methyl-N-[1-[5-(3,4-difluorophenylmethoxy)-pentyl]-4-piperidyl]-4H-3,1-benzothiazin-2-amine hydrogen fumarate (10). Starting with 674 mg (2.3 mmol) of bromo derivative 10.1 above and condensing them with 600 mg (2.3 mmol) of N-methyl-N-(4-piperidyl)-4H-3,1-benzothiazin-2-amine according to 1.2, 882 mg of crystals (yield: 65%) of formula 10 are prepared:

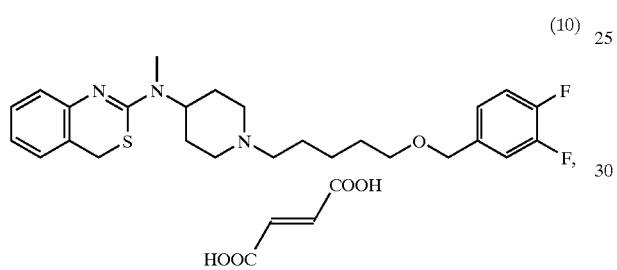
(10)

Empirical formula: $C_{30}H_{37}F_2N_3O_5S$; Molecular mass: 589.71; Off-white crystals; Melting point: 169° C.; NMR (DMSO d$_6$) δ: 1.2–1.8 (m, 8H); 1.8–2.07 (m, 2H); 2.3; (t, 2H); 2.4–2.6 (m, 2H); 3.01 (s, 3H); 3–3.25 (m, 2H); 3.43 (t, 2H); 3.95 (s, 2H); 4.25–4.55 (m, 1H); 4.44 (s, 2H); 6.58 (s, 2H); 6.96 (t, 2H); 7.03–7.27 (m, 3H); 7.3–7.45 (m, 2H); 11–13 (m, 2H).

EXAMPLE 11

N-Methyl-N-[1-[4-(3,4-difluorophenylmethoxy) butyl]-4-piperidyl]-4H-3,1-benzothiazin-2-amine Hydrogen Fumarate (11)

11.1) 1-(4-Bromobutoxymethyl)-3,4-difluorobenzene (11.1). The application of protocol 1.1 to 2 g (13.9 mmol) of 3,4-diflurobenzyl alcohol and to 15 g of 1,4-dibromobutane gives 2.80 g (yield: 72%) of compound of formula 11.1:

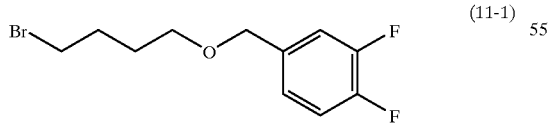
(11-1)

Empirical formula: $C_{11}H_{13}BrF_2O$; Molar mass: 279.13; Colorless oil; Boiling point: 120–125° C./0.3 mbar; NMR (CDCl$_3$) δ: 1.65–1.85 (m, 2H); 1.89–2.07 (m, 2H); 3.38–3.58 (m, 4H); 4.44 (s, 2H); 6.95–7.25 (m, 3H).

11.2) N-Methyl-N-[1-[4-(3,4-difluorophenylmethoxy)-butyl]-4-piperidyl]-4H-3,1-benzothiazin-2-amine hydrogen fumarate (11). The application of process 1.1 to 642 mg (2.3 mmol) of bromo derivative 11.1 above gives 790 mg (yield: 60%) of the derivative of formula 11:

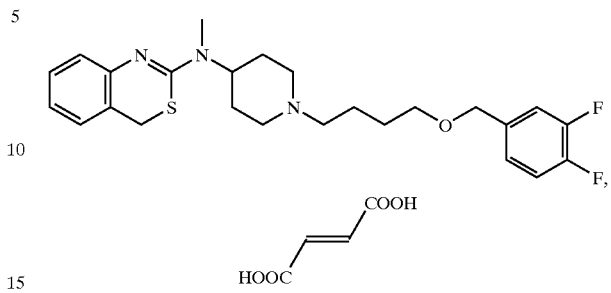
(11)

Empirical formula: $C_{29}H_{35}F_2N_3O_5S$; Molar mass: 575.68; White crystals; Melting point: 170° C.; NMR (DMSO d$_6$) δ: 1.45–1.76 (m, 6H); 1.78–2.08 (m, 2H); 2.3 (t, 2H); 2.4–2.6 (m, 2H); 3.02 (s, 3H); 3–3.22 (m, 2H); 3.45 (t, 2H); 3.95 (s, 2H); 4.25–4.55 (m, 1H); 4.45 (s, 2H); 6.58 (s, 2H); 6.94 (t, 2H); 7.1–7.25 (m, 3H); 7.3–7.45 (m, 2H); 10.5–12.5 (m, 2H).

EXAMPLE 12

N-Methyl-N-[1-[3-(3,4-difluorophenylmethoxy) propyl]-4-piperidyl]-4H-3,1-benzothiazin-2-amine Hydrogen Fumarate (12)

12.1) 1-(3-Bromopropyloxymethyl)-3,4-difluorobenzene (12.1). This compound was prepared according to protocol 1.1 in a yield of 21%, and is of formula 12.1:

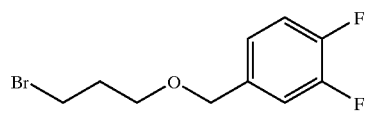
(12-1)

Empirical formula: $C_{10}H_{11}BrF_2O$; Molar mass: 265.10; Colorless oil; Boiling point: 92–94° C./0.18 mbar; NMR (CDCl$_3$) δ: 2.13 (q, 2H); 3.45–3.65 (m, 4H); 4.46 (s, 2H); 6.95–7.23 (m, 3H).

12.2) N-Methyl-N-[1-[3-(3,4-difluorophenylmethoxy)-propyl]-4-piperidyl]-4H-3,1-benzothiazin-2-amine hydrogen fumarate (12). The condensation of 330 mg (1.25 mmol) of compound 12.1 above according to protocol 1.2 gives 370 mg (yield: 52%) of powder of formula 12:

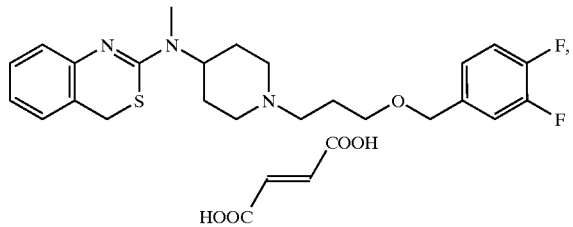
(12)

Empirical formula: $C_{28}H_{33}F_2N_3O_5S$; Molecular mass: 561.65; Pulverulent white crystals; Melting point: 168° C.; NMR (DMSO d$_6$) δ: 1.53–2.06 (m, 6H); 2.3 (t, 2H); 2.5–2.68 (m, 2H); 3.01 (s, 3H); 3–3.22 (m, 2H); 3.48 (t, 2H); 3.94 (s, 2H); 4.28–4.52 (m, 1H); 4.44 (s, 2H); 6.58 (s, 2H); 6.93 (t, 2H); 7.1–7.27 (m, 3H); 7.3–7.45 (m, 2H); 10.5–12.5 (m, 2H).

EXAMPLE 13

N-Methyl-N-[1-[4-[2-(3,4-difluorophenyl)ethoxy]butyl]-4-piperidyl]-4H-3,1-benzothiazin-2-amine Hydrogen Fumarate (13)

13.1) 3,4-Difluorophenethyl alcohol (13.1). A solution of 5 g (29 mmol) of methyl 3,4-difluorophenylacetate (prepared by Fischer reaction starting with the corresponding acid in a yield of 92%) in 30 ml of anhydrous THF is treated with 29 ml of a 2M solution of $LiAlH_4$ in THF at 0° C. After stirring for a further one hour, 30 ml of ethyl acetate are added dropwise, followed by 10 ml of water, and the mixture is stirred for 10 min at 25° C., dried over anhydrous sodium sulfate and the insoluble mineral is removed. The filtrate is evaporated to dryness and purified by flash chromotography, eluting with a 97/03 petroleum ether/ethyl acetate mixture. 3.6 g (yield: 77%) of alcohol of formula 13.1 are thus obtained:

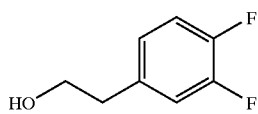
(13-1)

Empirical formula: $C_8H_8F_2O$; Molar mass: 158.15; Slightly amber-colored oil; NMR ($CDCl_3$) δ: 2.39 (s, 1H); 2.77 (t, 2H); 3.77 (t, 2H); 6.82–7.15 (m, 3H).

13.2) 1-[2-(4-Bromobutoxy)ethyl]-3,4-difluorobenzene 13.2. Starting with 1.2 g (7.6 mmol) of alcohol 13.1 above, by reaction according to process 1.1, the compound of formula 13.2 is prepared in a yield of 78%:

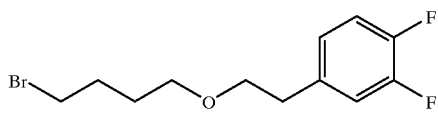
(13-2)

Empirical formula: $C_{12}H_{15}BrF_2O$ Molar mass: 293.16; Slightly amber-colored oil; NMR ($CDCl_3$) δ: 1.6–1.78 (m, 2H); 1.81–2.04 (m, 2H); 2.83; (t, 2H); 3.36–3.52 (m, 4H); 3.61 (t, 2H); 6.85–7.2 (m, 3H).

13.3) N-Methyl-N-[1-[4-[2-(3,4-difluorophenyl)ethoxy]-butyl]-4-piperidyl]-4H-3,1-benzothiazin-2-amine hydrogen fumarate (13). N-alkylation of 600 mg (2.3 mmol) of N-methyl-N-(4-piperidyl)-4H-3,1-benzothiazin-2-amine with 674 mg of bromo compound 13.2 above gives 795 mg (yield: 65%) of compound of formula 13:

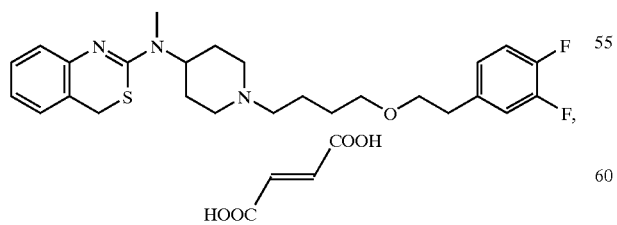
(13)

Empirical formula: $C_{30}H_{37}F_2N_3O_5S$; Molar mass: 589.71; Off-white crystals; Melting point: 163° C.; NMR (DMSO $d_6$) δ: 1.4–1.78 (m, 6H); 1.78–2.08 (m, 2H); 2.3 (t, 2H); 2.42–2.58 (m, 2H); 2.80 (t, 2H); 3.02 (s, 3H); 3–3.2 (m, 2H); 3.38 (t, 2H); 3.56 (t, 2H); 3.94 (s, 2H); 4.4 (m, 1H); 6.57 (s, 2H); 6.94 (t, 2H); 7.1–7.42 (m, 5H); 11–13 (m, 2H).

EXAMPLE 14

N-Methyl-N-[1-[3-[2-(3,4-difluorophenyl)ethoxy]propyl]-4-piperidyl]-4H-3,1-benzothiazin-2-amine Hydrogen Fumarate (14)

14.1) 1-[2-(3-Bromopropyloxy)ethyl]-3,4-difluorobenzene (14.1). Using the process of Example 1.1, the compound of formula 14.1 is similarly prepared in a yield of 32%:

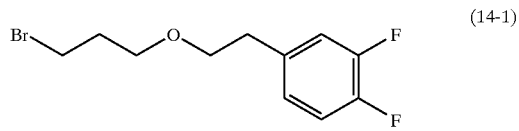
(14-1)

Empirical formula: $C_{11}H_{13}BrF_2O$; Molar mass: 279.13; Colorless oil; Boiling point: 85–90° C./0.13 mbar; NMR ($CDCl_3$) 67 : 2.05 (q, 2H); 2.7–2.9 (m, 4H); 3.4–3.7; (m, 4H); 6.8–7.2 (m, 3H).

14.2) N-Methyl-N-[1-[3-[2-(3,4-difluorophenyl)ethoxy]-propyl]-4-piperidyl]-4H-3,1-benzothiazin-2-amine hydrogen fumarate (14). Condensation of 430 mg (1.53 mmol) of bromo derivative 14.1 above according to procedure 1.2 gives 512 mg (yield: 58%) of derivative of formula 14:

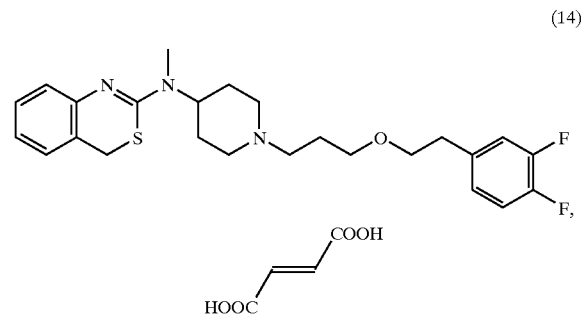
(14)

Empirical formula: $C_{29}H_{35}F_2N_3O_5S$; Molar mass: 575.68; Pulverulent white crystals; Melting point: 162° C.; NMR (DMSO $d_6$) δ: 1.55–2.1 (m, 6H); 2.31 (t, 2H); 2.4–2.57 (m, 2H); 2.80 (t, 2H); 3.02 (s, 3H); 3–3.18 (m, 2H); 3.42 (t, 2H); 3.57 (t, 2H); 3.95 (s, 2H); 4.4 (m, 1H); 6.58 (s, 2H); 6.94 (t, 2H); 7.02–7.45 (m, 5H); 9–11 (m, 2H).

EXAMPLE 15

N-Methyl-N-1-[5-(4-methoxyphenylmethoxy)pentyl]-4-piperidyl]-4H-3,1-benzothiazin-2-amine Hydrogen Fumarate (15)

15.1) 1-(5-Bromopentyloxymethyl)-4-methoxybenzene (15.1). Prepared according to method 1.1 from 2 g (15 mmol) of p-methoxybenzyl alcohol in a yield of 90%, and having the formula 15.1:

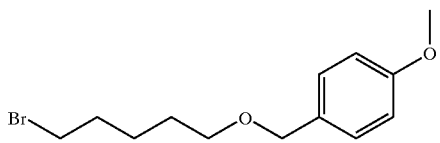

(15-1)

Empirical formula: $C_{13}H_{19}BrO_2$; Molar mass: 287.20; Slightly amber-colored oil; NMR (CDCl$_3$) δ: 1.4–1.75 (m, 4H); 1.75–1.98 (m, 2H); 3.32–3.5 (m, 4H); 3.80 (s, 3H); 4.44 (s, 2H); 6.88 (d, 2H); 7.26 (d, 2H).

15.2) N-Methyl-N-[1-[5-(4-methoxyphenylmethoxy)pentyl]-4-piperidyl]-4H-3,1-benzothiazin-2-amine hydrogen fumarate (15). This derivative is prepared according to process 1.2 starting with 660 mg (2.3 mmol) of the preceding bromo derivative. 718 mg (yield: 53%) of powder of formula 15 are obtained:

(15)

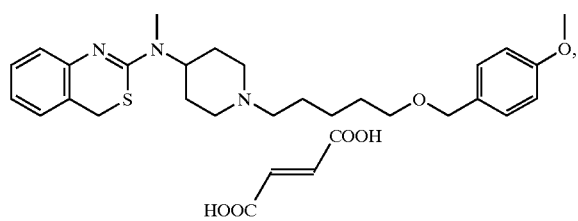

Empirical formula: $C_{31}H_{41}N_3O_6S$; Molar mass: 583.75; White crystals; Melting point: 163° C.; NMR (DMSO d$_6$) δ: 1.22–1.82 (m, 8H); 1.84–2.1 (m, 2H); 2.25–2.68 (m, 4H); 3 (s, 3H); 3.08–3.24 (m, 2H); 3.38 (t, 2H); 3.74 (s, 3H); 3.94 (s, 2H); 4.3–4.55 (m, 1H); 4.36 (s, 2H); 6.56 (s, 2H); 6.82–7.06 (m, 4H); 7.08–7.32 (m, 4H); 12–14 (m, 2H).

EXAMPLE 16

N-Methyl-N-[1-[4-(4-methoxyphenylmethoxy)butyl]-4-piperidyl]-4H-3,1-benzothiazin-2-amine Hydrogen Fumarate (16)

16.1) 1-(4-Bromobutyloxymethyl)-4-methoxybenzene (16.1). This compound is prepared in a yield of 70% as described in 1.1, and has the formula 16.1:

(16-1)

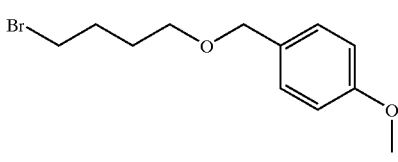

Empirical formula: $C_{12}H_{17}BrO_2$; Molar mass: 273.18; Colorless oil; NMR (CDCl$_3$) δ: 1.64–1.8 (m, 2H); 1.83–2.08 (m, 2H); 3.35–3.54 (m, 4H); 3.81 (s, 3H); 4.44 (s, 4H); 6.87 (d, 2H); 7.26 (d, 2H).

16.2) N-Methyl-N-[1-[4-(4-methoxyphenylmethoxy)butyl]-4-piperidyl]-4H-3,1-benzothiazin-2-amine hydrogen fumarate. Reaction of 630 mg (2.3 mmol) of bromo derivative 16.1 above with 600 mg (2.3 mmol) of N-methyl-N-(4-piperidyl)-4H-3,1-benzothiazine-2-amine gives, after salification, 849 mg (yield: 64%) of N-alkyl compound of formula 16:

(16)

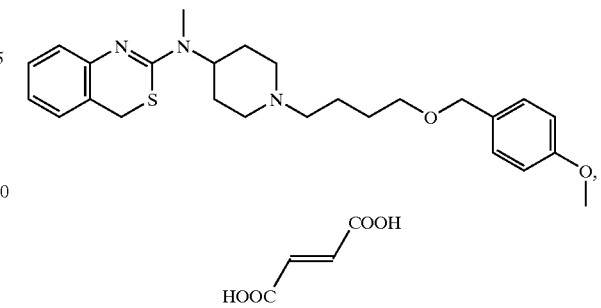

Empirical formula: $C_{30}H_{39}N_3O_6S$; Molar mass: 569.72; White crystals; Melting point: 165° C.; NMR (DMSO d$_6$) δ: 1.4–2.06 (m, 8H); 2.34 (t, 2H); 2.45–2.62 (m, 2H); 2.99 (s, 3H); 3.04–3.2 (m, 2H); 3.38 (t, 2H); 3.72 (s, 3H); 3.92 (s, 2H); 4.28–4.52 (m, 1H); 4.35 (s, 2H); 6.55 (s, 2H); 6.8–7 (m, 4H); 7.05–7.28 (m, 4H); 9–11 (m, 2H).

EXAMPLE 17

N-Methyl-N-[1-[3-(4-methoxyphenylmethoxy)propyl]-4-piperidyl]-4H-3,1-benzothiazin-2-amine Hydrogen Fumarate (17)

17.1) 1-(3-Bromopropyloxymethyl)-4-methoxybenzene (17.1). Application of protocol 1.1 to 3 g (22 mmol) of 4-methoxybenzyl alcohol gives, in a yield of 33%, the compound of formula 17.1:

(17-1)

Empirical formula: $C_{11}H_{15}BrO_2$; Molar mass: 259.51; Slightly amber-colored oil; NMR (CDCl$_3$) δ: 2.11 (q, 2H); 3.45–3.62 (m, 4H); 3.79 (s, 3H); 4.44 (s, 2H); 6.86 (d, 2H); 7.26 (d, 2H).

a) N-Methyl-N-[1-[3-(4-methoxyphenylmethoxy)propyl]-4-piperidyl]-4H-3,1-benzothiazin-2-amine (17). Again according to the process of Example 1.2, 910 mg (yield: 71%) of the compound of formula 17 is prepared starting with 620 mg of the corresponding bromo derivative 17.1:

(17)

Empirical formula: $C_{29}H_{37}N_3O_6S$; Molar mass: 555.70; White crystals; Melting point: 166° C.; NMR (DMSO d$_6$) δ: 1.58–2.08 (m, 6H); 2.34 (t, 2H); 2.6 (t, 2H); 3.03 (s, 3H); 3.04–3.23 (m, 2H); 3.44 (t, 2H); 3.76 (s, 3H); 3.96 (s, 2H);

4.39 (s, 2H); 4.2–4.6 (m, 1H); 6.59 (s, 2H); 6.84–7.03 (m, 4H); 7.1–7.32 (m, 4H); 8.5–11 (m, 2H).

EXAMPLE 18

N-Methyl-N-[1-[4-[2-(4-methoxyphenyl)ethoxy]butyl]-4-piperidyl]-4H-3,1-benzothiazin-2-amine Hydrogen Fumarate (18)

18.1) 1-[2-(4-Bromobutyloxy)ethyl]-4-methoxybenzene (18.1). Working as in Example 1.1, starting with 2 g (13.1 mmol) of 4-methoxyphenethyl alcohol, 3.3 g (yield: 88%) of the bromo derivative having the formula 18.1 are prepared:

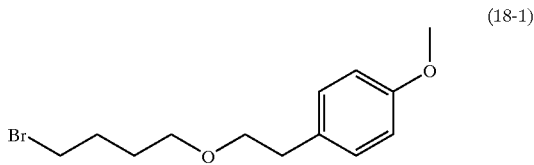
(18-1)

Empirical formula: $C_{13}H_{19}BrO_2$; Molar mass: 287.19; Colorless oil; NMR (CDCl$_3$) δ: 1.6–1.8 (m, 2H); 1.8–2 (m, 2H); 2.80 (t, 2H); 3.32–3.5 (m, 4H); 3.57 (t, 2H); 3.77 (s, 3H); 6.81 (d, 2H); 7.12 (d, 2H).

18.2) N-Methyl-N-[1-[4-[2-(4-methoxyphenyl)ethoxy]butyl]-4-piperidyl]-4H-3,1-benzothiazin-2-amine hydrogen fumarate (18). By applying the process described in Example 1.1, the compound of formula 18 is similarly prepared, in a yield of 63% starting with 846 mg of bromo derivative 18.1:

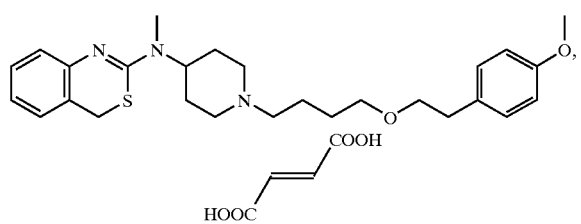
(18)

Empirical formula: $C_{31}H_{41}N_3O_6S$; Molar mass: 583.726; White crystals; Melting point: 156° C.; NMR (DMSO d$_6$) δ: 1.42–2.1 (m, 8H); 2.36 (t, 2H); 2.45–2.63 (m, 2H); 2.74 (t, 2H); 3.03 (s, 3H); 3.04–3.22 (m, 2H); 3.39 (t, 2H); 3.53 (t, 2H); 3.72 (s, 3H); 3.96 (s, 2H); 4.43 (m, 1H); 6.58 (s, 2H); 6.8–7.03 (m, 4H); 7.1–7.24 (m, 4H); 11–13 (m, 2H).

EXAMPLE 19

N-Methyl-N-[1-[3-[2-(4-methoxyphenyl)ethoxy]propyl]-4-piperidyl]-4H-3,1-benzothiazin-2-amine Hydrogen Fumarate (19)

19.1) 1-[2-(3-Bromopropyloxy)ethyl]-4-methoxybenzene (19.1). Application of process 1.1 to 4-methoxy-phenethyl alcohol gives, in a yield of 22%, the compound of formula 19.1:

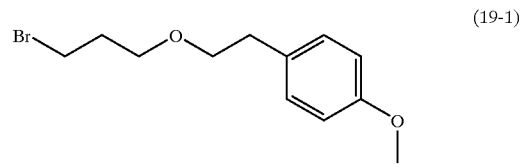
(19-1)

Empirical formula: $C_{12}H_{17}BrO_2$; Molar mass: 273.17; Colorless oil; Boiling point: 103–105° C./0.08 mbar; NMR (CDCl$_3$) δ: 2.1 (q, 2H); 2.83 (t, 2H); 3.42–3.68 (m, 6H); 3.8 (s, 3H); 6.85 (d, 2H); 7.15 (d, 2H). 19.2) N-Methyl-N-[1-[3-[2-(4-methoxyphenyl)ethoxy]-propyl]-4-piperidyl]-4H-3,1-benzothiazin-3-amine hydrogen fumarate (19). By reacting 660 mg (2.4 mmol) of the above bromo derivative 19.1 according to protocol 1.2, 915 mg (yield: 69%) of compound of formula 19 are prepared:

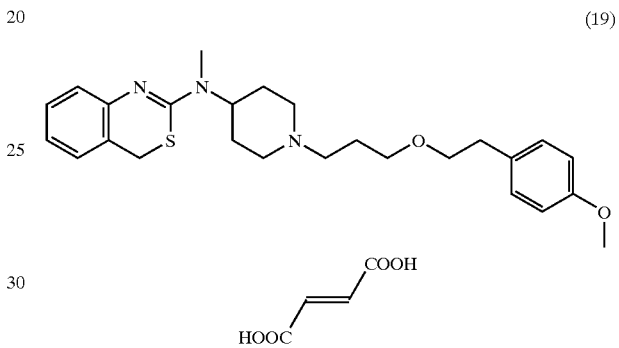
(19)

Empirical formula: $C_{30}H_{39}N_3O_6S$; Molar mass: 569.70; White crystals; Melting point: 155° C.; NMR (DMSO d$_6$) δ: 1.52–2.03 (m, 6H); 2.28 (t, 2H); 2.4–2.55 (m, 2H); 2.71 (t, 2H); 3 (s, 3H); 3–3.2 (m, 2H) 3.39 (t, 2H); 3.5 (t, 2H); 3.69 (s, 3H); 3.99 (s, 2H); 3.37 (m, 1H); 6.56 (s, 2H); 6.73–6.98 (m, 4H); 7.02–7.22 (m, 4H); 8.5–10.5 (m, 2H).

EXAMPLE 20

N-Methyl-N-[1-[2-[2-(4-methoxyphenyl)ethoxy]ethyl]-4-piperidyl]-4H-3,1-benzothiazin-2-amine Hydrogen Fumarate (20)

20.1) 2-[2-(4-Methoxyphenyl)ethoxy]ethanol (20.1). Working as described in Example 4.1, but starting with 5 g (32.8 mmol) of 2-(4-methoxyphenyl)ethanol, 2.6 g (yield: 40%) of compound of formula 20.1 are prepared:

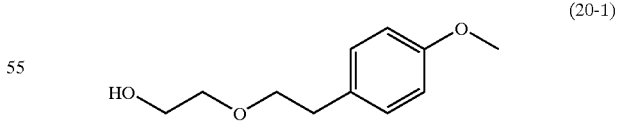
(20-1)

Empirical formula: $C_{11}H_{16}O_3$; Molar mass: 196.24; Colorless oil; NM (CDCl$_3$) δ: 1.89 (s,. 1H); 2.87 (t, 2H); 3.58 (t, 2H); 3.63–3.75 (m, 4H); 3.81 (s, 3H); 6.86 (d, 2H); 7.36 (d, 2H).

20.2) 2-[2-(4-Methoxyphenyl)ethoxy]ethyl mesylate (20.2). Reaction of 0.52 ml (6.7 mmol) of mesyl chloride with 1.2 g of the above alcohol 20.1 according to 4.2 gives 1.56 g (yield: 93%) of compound of formula 20.2:

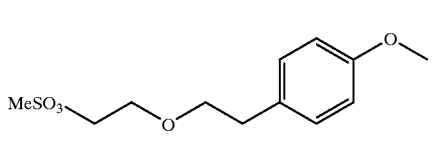

Empirical formula: $C_{12}H_{18}O_5S$; Molar mass: 274.32; Pale yellow liquid; NMR (CDCl$_3$) δ: 2.86 (t, 2H); 2.96 (s, 3H); 3.65–3.75 (m, 4H); 3.80 (s, 3H); 4.32–4.42 (m, 2H); 6.85 (d, 2H); 7.15 (d, 2H).

20.3) N-Methyl-N-[1-[2-[2-(4-methoxyphenyl)ethoxy]-ethyl]-4-piperidyl]-4H-3,1-benzothiazin-2-amine hydrogen fumarate (20). Application of process 1.2 to 800 mg (2.9 mmol) of the above mesylate 20.2 gives 615 mg (yield: 41%) of compound of formula 20:

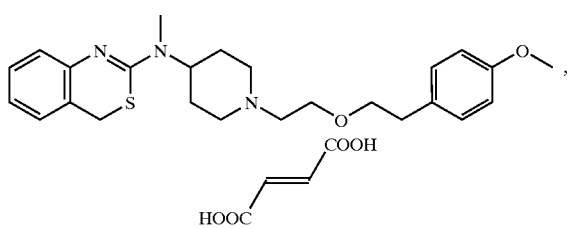

Empirical formula: $C_{29}H_{37}N_3O_6S$; Molar mass: 555.67; White crystals; Melting point: 152–3° C.; NMR (DMSO d$_6$) δ: 1.5–1.63 (m, 2H); 1.75–1.92 (m, 2H); 2.52 (t, 2H); 2.63 (t, 2H); 2.74 (t, 2H); 3.02 (s, 3H); 3–31 (m, 2H); 3.5–3.6 (m, 4H); 3.70 (s, 3H); 3.94 (s, 2H); 4.33 (m, 1H); 6.6 (s, 2H); 6.84 (d, 2H); 6.93 (q, 2H); 7.1–7.2 (m, 4H); 10–12 (m, 2H).

EXAMPLE 21

N-Methyl-N-[1-(2-phenylmethoxyethyl)-4-piperidyl]-4H-3,1-benzothiazin-2-amine Hydrogen Fumarate (21)

21.1) 2-Phenylmethoxyethyl mesylate (21.1). Starting with 2 g (13.1 mmol) of 2-benzyloxyethanol and by adapting the process described in Example 4.2, 3.02 g (yield: 94%) of an oil of formula 21.1 are prepared:

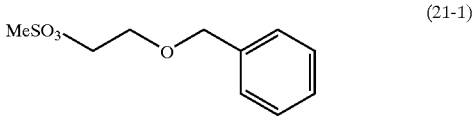

Empirical formula: $C_{10}H_{14}O_4S$; Molar mass: 230.27; Pale yellow oil; NMR (CDCl$_3$) δ: 3.02 (s, 3H); 3.65–3.77 (m, 2H); 4.34–4.43 (m, 2H); 4.56 (s, 2H); 7.32 (s, 5H).

21.2) N-Methyl-N-[1-(2-phenylmethoxyethyl)-4-piperidyl]-4H-3,1-benzothiazin-2-amine hydrogen fumarate (21). The action of 580 mg (2.5 mmol) of the above mesylate 21.1 with 600 mg (2.3 mmol) of N-methyl-N-[4-piperidyl]-4H-3,1-benzothiazin-2-amine according to process 1.2 gives 870 mg (yield: 74%) of powder of formula 21:

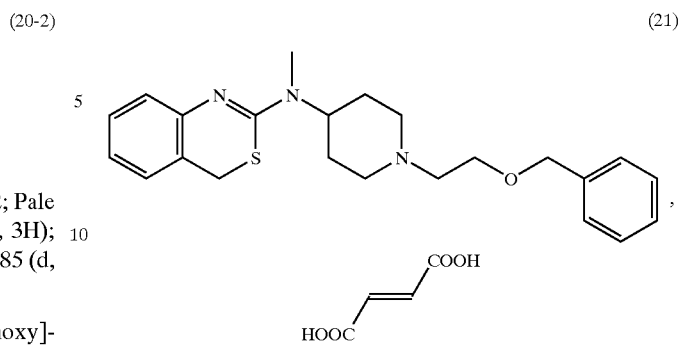

Empirical formula: $C_{27}H_{33}N_3O_5S$; Molar mass: 511.62; White crystals; Melting point: 166–7° C.; NMR (DMSO d$_6$) δ: 1.52–2.02 (m, 4H); 2.32 (t, 2H); 2.71; t, 2H); 3 (s, 3H); 3–3.17 (m, 2H); 3.59 (t, 2H); 3.93; (s, 2H); 4.35 (m, 1H); 4.83 (s, 2H); 6.58 (s, 2H); 6.92; (t, 2H); 7.09–7.2 (m, 2H); 7.2–7.4 (m, 5H); 11–13 (m, 2H).

EXAMPLE 22

N-Methyl-N-[1-[3-(2-phenylethoxy)propyl]-4-piperidyl]-4H-3,1-benzothiazin-2-amine Hydrogen Fumarate (22)

22.1) 1-(2-Phenylethoxy)-3-chloropropane (22.1). By working starting with 20 g (0.164 mmol) of phenethyl alcohol according to the process described in Example 6.1, 24.32 g (yield: 75%) of compound of formula 22.1 are prepared:

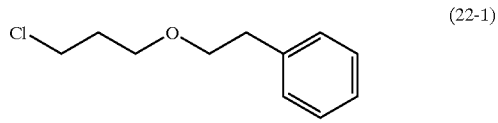

Empirical formula: $C_{11}H_{15}ClO$; Molecular mass: 198.68; Colorless oil; Boiling point: 85–90° C./0.15 mbar; NMR (CDCl$_3$) δ: 2.07 (q, 2H); 2.88 (t, 2H); 3.5–3.68 (m, 4H); 7.17–7.3 (m, 5H).

22.2) N-Methyl-N-[1-[3-(2-phenylethoxy)propyl]-4-piperidyl]-4H-3,1-benzothiazin-2-amine hydrogen fumarate (22). By condensation of 523 mg (2.63 mmol) of the above chloro derivative (22.1) with 665 mg (2.51 mmol) of N-methyl-N-(4-piperidyl)-4H-3,1-benzothiazin-2-amine, according to the protocol described in Example 1.2, 698 mg (yield: 51%) of compound of the following formula are prepared:

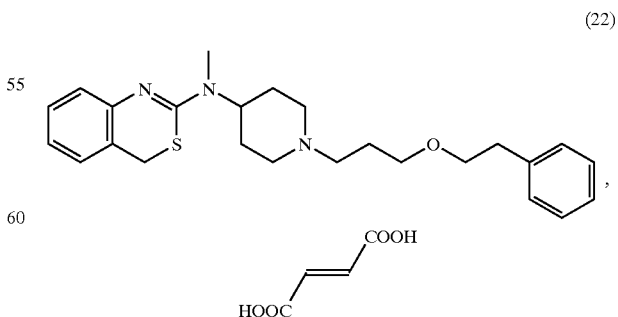

Empirical formula: $C_{29}H_{37}N_3O_5S$; Molar mass: 539.67; Pulverulent white crystals; Melting point: 166° C.; NMR (DMSO d$_6$) δ: 1.6–1.73 (m, 4H); 1.78–1.92 (m, 2H); 2.17 (t, 2H); 2.45 (t, 2H); 2.8 (t, 2H); 3.02 (s, 3H); 3–3.1 (m, 2H); 3.42 (t, 2H); 3.57 (t, 2H); 3.94 (s, 2H); 4.35 (m, 1H); 6.59 (s, 2H); 6.88–6.97 (m, 2H); 7.1–7.5 (m, 7H); 12–14 (m, 2H).

EXAMPLE 23

N-Methyl-N-[1-[2-hydroxy-3-(4-fluorophenylmethoxy)-propyl]-4-piperidyl]-4H-3,1-benzothiazin-2-amine Hemifumarate (23)

23.1) 1-(4-Fluorophenylmethoxy)-2,3-epoxypropane (21.1). A mixture of 55 ml of 50% (by weight) caustic soda, 1.38 g (4 mmol) of tetrabutylammonium bisulfate and 78 ml of epichlorohydrin is stirred vigorously at 25° C. and then treated over 10–15 minutes (dropwise) with 12.7 g (0.1 mol) of 4-fluorobenzyl alcohol, while keeping the temperature below 28° C. The reaction is continued for a further 3 h 30 min and the mixture is the extracted with ether, washed with sodium bicarbonate, with water and with brine, and dried over anhydrous sodium sulfate. After removing the mineral salt, the filtrate is evaporated to dryness to give a pale oil which is rectified under vacuum and of formula 23.1 (yield: 75%):

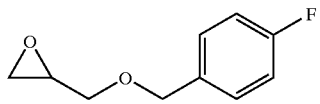
(23-1)

Empirical formula: C$_{10}$H$_{11}$FO$_2$; Molar mass: 182.19; Colorless oil; Boiling point: 90–92° C./0.15 mbar; NMR (CDCl$_3$) δ: 2.62 (q, 1H); 2.81 (t, 1H); 3.15–3.25 (m, 1H); 3.32–3.48 (m, 1H); 3.78 (dd, 1H); 4.55 (q, 2H); 7.03 (t, 2H); 7.22–7.34 (m, 2H).

23.2) N-Methyl-N-[1-[2-hydroxy-3-(4-fluorophenyl-methoxy)propyl]-4-piperidyl]-4H-3,1-benzothiazin-2-amine hemifumarate (23). A solution of 580 mg (3.2 mmol) of the above epoxide 23.1 in 8 ml of ethanol is treated with 800 mg (3.06 mmol) of N-methyl-N-(4-piperidyl)-4H-3,1-benzothiazin-2-amine and stirred overnight at 25° C. The reaction mixture is evaporated to dryness and the residue is then purified by flash chromatography, eluting with a 97.5/2.25/0.25 CH$_2$Cl$_2$/CH$_3$OH/NH$_4$OH mixture to give a pale yellow oil (m=1.20 g; yield: 85%). The above base is salified in the usual manner. The hemifumarate of formula 23 precipitates (m=1.05 g; overall yield: 68%).

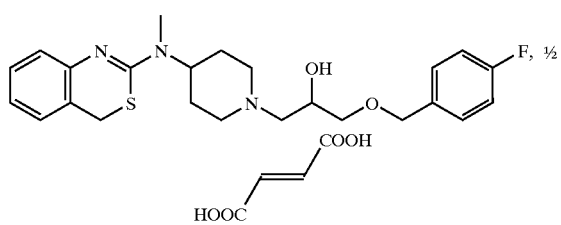
(23)

Empirical formula: C$_{26}$H$_{32}$FN$_3$O$_4$S; Molar mass: 501.60; Pulverulent white crystals; Melting point: 155–156° C.; NMR (DMSO d$_6$) δ: 1.5–1.63 (m, 2H); 1.75–1.85 (m, 2H); 2.17–2.3 (m, 2H); 2.3–2.52 (m, 2H); 3.02 (s, 3H); 3–3.09 (m, 2H); 2.8–3.5 (m, 1H); 3.3–3.47 (m, 2H); 3.75–3.85 (m, 1H); 3.94 (s, 2H); 4.32 (m, 1H); 4.48 (s, 2H); 6.58 (s, 1H); 6.85–6.98 (m, 2H); 7.1–7.23 (m, 4H); 7.35–7.42 (m, 2H); 11–13 (m, 1H).

EXAMPLE 24

N-Methyl-N-[1-[2-hydroxy-3-[2-(4-methoxyphenyl)ethoxy]-propyl]-4-piperidyl]-4H-3,1-benzothiazin-2-amine Hydrogen Fumarate (24)

24.1) 1-[2-(4-methoxyphenyl)ethoxy]-2,3-epoxypropane (24.1). By condensation of 4.8 g (31.5 mmol) of 4-methoxyphenethyl alcohol in a mixture of 25 ml of epichlorohydrin and 18 ml of 50% caustic soda and 430 mg of Bu$_4$NHSO$_4$ according to process 23.1, 4.42 g (yield: 67%) of glycidyl ether of formula 24.1 are prepared:

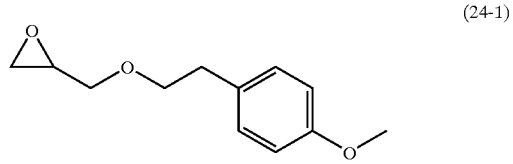
(24-1)

Empirical formula: C$_{12}$H$_{16}$O$_3$; Molecular mass: 208.25; Colorless oil; Boiling point: 130–135° C./0.25 mbar; NMR (CDCl$_3$) δ: 2.6 (s, 1H); 2.78 (s, 1H); 2.79–2.91 (m, 2H); 3 (s, 1H); 3.34–3.5 (m, 1H); 3.5–3.89 (m, 3H); 3.9; (s, 3H); 6.83 (d, 2H); 7.14 (d, 2H).

15 24.2) N-Methyl-N-[1-[2-hydroxy-3-[2-(4-methoxyphenyl)-ethoxy]propyl]-4-piperidyl]-4H-3,1-benzothiazin-2-amine hydrogen fumarate (24). Using the process of Example 23.2, but starting with 620 mg (2.9 mmol) of the above glycidyl ether (24.1), 692 mg (yield: 41%) of compound of formula 24 are prepared:

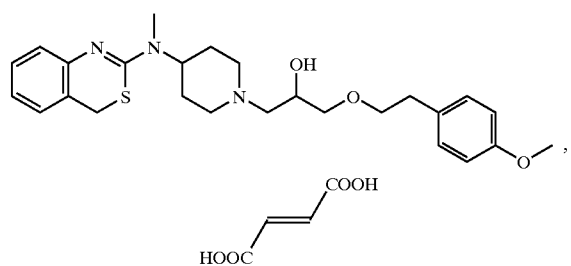
(24)

Empirical formula: C$_{30}$H$_{39}$N$_3$O$_7$S; Molar mass: 585.70; Off-white crystals; Melting point: 132–3° C.; NMR (DMSO d$_6$) δ: 1.5–1.67 (m, 2H); 1.8–1.98 (m, 2H); 2.25–2.48 (m, 4H); 2.74 (t, 2H); 3.02 (s, 3H); 3.08 (t, 2H); 2.9–3.2 (m, 1H); 3.3–3.39 (m, 2H); 3.57 (t, 2H); 3.71 (s, 3H); 3.73–3.78 (m, 1H); 3.94 (s, 2H); 4.36 (m, 1H); 6.59 (s, 2H); 6.84 (d, 2H); 6.88–6.97 (m, 2H); 7.06–7.21 (m, 4H); 10–12 (m, 2H).

EXAMPLE 25

6,N-Dimethyl-N-[1-[3-[2-(4-fluorophenyl)ethoxy]propyl]-4-piperidyl]-4H-3,1-benzothiazin-2-amine Hydrogen Fumarate (25)

25.1) 2-Amino-5-methylbenzyl alcohol (25.1): A suspension of 3.80 g (0.1 mol) of LiAlH$_4$ in 200 ml of dry THF, cooled on an ice bath, is treated dropwise with a solution of 17.95 g (0.1 mol) of ethyl 2-amino-5-methylbenzoate dissolved in 150 ml of THF. The mixture is stirred for a further 1 h at this temperature and is then left to warm to 25° C. and stirring is continued for a further 4 h at 25° C. The mixture is cooled to 0° C. and treated dropwise with 30 ml of ethyl acetate, 10 ml of water are then added dropwise, the mixture is dried over anhydrous sodium sulfate and the insoluble material is filtered off. The mixture is evaporated to dryness to give an amber-colored oil, which is slurried in isopropyl ether to give 9.42 g (yield: 68%) of powder of formula 25.1:

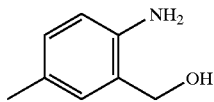
(25-1)

Empirical formula: $C_8H_{11}NO$; Molar mass: 137.18; Beige-colored powder; Melting point: 124° C.; NMR (DMSO $d_6$) δ: 2.13 (s, 3H); 4.33 (d, 2H); 4.68 (s, 2H); 4.95 (t, 1H); 6.51 (d, 1H); 6.7–6.8 (m, 1H); 6.86 (s, 1H).

25.2) 1-[3-[2-(4-Fluorophenyl)ethoxy]propyl]-4-piperidone (25.2). A solution of 17.5 g (81 mmol) of 1-fluoro-4-[2-(3-chloropropyloxy)ethyl]benzene (prepared according to Example 22.1) in 175 ml of DMF is treated with stirring, at 25° C., with 10.4 ml of 1,4-dioxa-8-azaspiro[4,5]decane (11.6 g or 81 mmol) and 12.4 g (85 mmol) of an intimately ground mixture of 98/02 $K_2CO_3$/KI, and the mixture is then heated for 5 h at 80° C. The insoluble material is removed by filtration and the solution obtained is evaporated to dryness under vacuum. The residue is formed of the protected amino ketone of formula 25.2.1, which is not isolated.

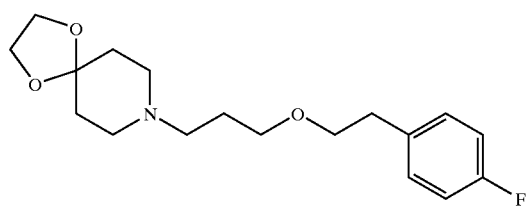
(25-2-1)

This compound is treated with 160 ml of 6N hydrochloric acid and heated for 2 h at 100° C. with stirring. After cooling to 25° C., the unsalifiable materials are extracted with $CH_2Cl_2$ and the aqueous phase is separated out, cooled to 0° C. and basified with 10N sodium hydroxide to pH 12–13. The amino ketone is extracted with $CH_2Cl_2$ and then washed with water and with brine, dried over anhydrous sodium sulfate, filtered and evaporated to dryness: 17.3 g of crude residue of formula 25.2 are obtained:

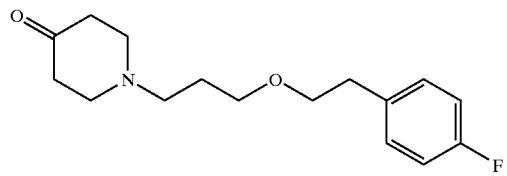
(25-2)

Empirical formula: $C_{16}H_{22}FNO_2$; Molecular mass: 279.35; Slightly orange-colored viscous oil; NMR (CDCl$_3$) δ: 1.5–1.85 (m, 2H); 2.36–2.58 (m, 6H); 2.72 (t, 4H); 2.85 (t, 2H); 3.5 (t, 2H); 3.61 (t, 2H); 6.91–7 (m, 2H); 7.1–7.2 (m, 2H).

25.3) 4-Methylamino-1-[3-[2-(4-fluorophenyl)ethoxy]propyl)piperidine dihydrochloride (25.3). A solution of 14.7 g (52.6 mmol) of the above keto amine (25.2) in 150 ml of $CH_2Cl_2$ is treated with 3.5 g (52.6 mmol) of methylamine hydrochloride, and methanol is then added until dissolution is complete. After stirring for 3 h at 25° C., the mixture is cooled on an ice bath and 14.5 g (68.5 mmol) of sodium borohydride triacetate are added portionwise, and finally 3 ml of acetic acid are added dropwise. Stirring is continued overnight at 25° C. The reaction mixture is poured onto ice and basified to pH 12–13. The base freed is extracted in the usual manner to give a greenish oil. After dissolution in 70 ml of absolute ethanol, the hydrochloride is prepared at 0C by adding 2.5 N hydrochloric ethanol solution. The salt crystallizes after scratching and is recovered by filtration to give 13.6 g (yield: 70%) of crystals of formula 25.3:

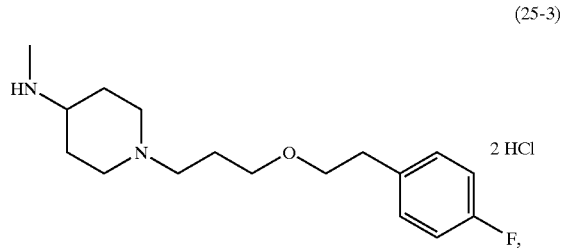
(25-3)

Empirical formula: $C_{17}H_{29}Cl_2FN_2O$; Molar mass: 367.34; Off-white crystals; NMR (DMSO $d_6$) δ: 1.9–2.05 (m, 4H); 2.12–2.3 (m, 2H); 2.50 (s, 3H); 2.8 (t, 2H); 2.84–3 (m, 4H); 3.17 (m, 1H); 3.45 (t, 2H); 3.5–3.6 (m, 4H); 7.11 (t, 2H); 7.28 (dd, 2H); 9.42 (m, 2H); 10.7 (m, 1H).

25.4) 1-[1-[3-[2-(4-Fluorophenyl)ethoxy]propyl]-4-piperidyl]-1-methyl-3-(2-hydroxymethyl-4-methyl-phenyl)thiourea hydrochloride (25.4). 0.39 ml (580 mg, 5 mmol) of thiophosgene is added to a suspension of 700 mg (5 mmol) of $K_2CO_3$ in 10 ml of $CH_2Cl_2$ cooled on an ice bath and placed under a stream of nitrogen, followed by dropwise addition of a solution of 1.47 g (5 mmol) of the above diamine (25.3 in the form of the free base) over 20 minutes. After stirring for a further one hour, the insoluble material is removed by filtration and the filtrate containing the intermediate compound (25.4.1):

(25-4-1)

$$\left[ \begin{array}{c} \text{Cl} \overset{\text{S}}{\underset{}{\parallel}} \text{C} - \text{N(CH}_3\text{)} - \text{piperidinyl-N-CH}_2\text{CH}_2\text{CH}_2\text{-O-CH}_2\text{CH}_2\text{-C}_6\text{H}_4\text{-F} \end{array} \right]$$

is added dropwise to a solution of 690 mg (5 mmol) of 2-amino-5-methylbenzyl alcohol in 30 ml of $CH_2Cl_2$ and stirring is continued for 1 h. The reaction mixture is evaporated to dryness to give a residue which, when slurried in ether, gives 1.86 g (yield: 73%) of compound of formula 25.4:

(25-4)

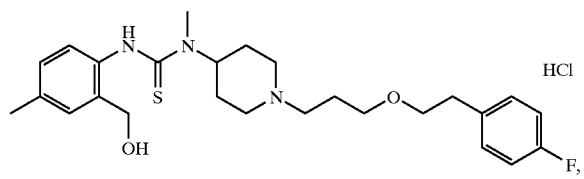

Empirical formula: $C_{26}H_{37}ClFN_3O_2S$; Molecular mass: 510.09; Cream-colored crystals; Melting point: 112–115° C.; NMR (CDCl$_3$) δ: 1.9–2.13 (m, 4H); 2.33 (s, 3H); 2.5–2.68 (m, 2H); 2.72–2.85 (m, 4H); 2.89–2.98 (m, 2H); 3.2 (s, 3H); 3.40–3.63 (m, 5H); 3.88 (t, 2H); 4.58 (s, 2H); 5.73 (m, 1H); 6.9–7.03 (m, 3H); 7.08–7.24 (m, 4H); 7.53 (d, 1H); 8.31 (s, 1H); 12 (m, 1H).

25.5) 6,N-Dimethyl-N-[1-[3-[2-(4-fluorophenyl)-ethoxy]propyl]-4-piperidyl]-4H-3,1-benzothiazin-2-amine hydrogen fumarate (25). A mixture of 1.75 g (3.43 mmol) of the above hydroxythiourea (25.4) in 4 ml of concentrated hydrochloric acid is heated at 50° C. for 20 minutes. The reaction mixture is then poured onto crushed ice and basified with sodium hydroxide to pH 10–12, and then extracted with ethyl acetate, washed with water and with brine, dried over anhydrous sodium sulfate, filtered and evaporated to dryness to give 1.39 g (yield: 82%) of an oil of formula 25.5 which crystallizes:

(25-5)

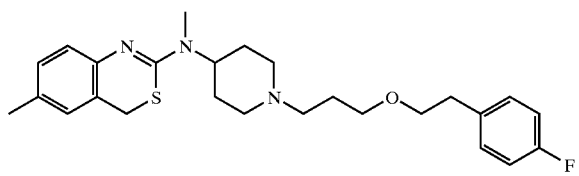

Empirical formula: $C_{26}H_{34}FN_3OS$; Molecular mass: 455.62; Beige-colored crystals; Melting point: 70° C.; NMR (CDCl$_3$) δ: 1.65–1.93 (m, 6H); 2–2.1 (m, 2H); 2.3 (s, 3H); 2.39 (t, 2H); 2.84 (t, 2H); 2.92–2.98 (m, 2H); 3.01 (s, 3H); 3.47 (t, 2H); 3.6 (t, 2H); 3.81 (s, 2H); 4.37 (m, 1H); 6.87 (s, 1H); 6.92–7.05 (m, 4H); 7.12–7.2 (m, 2H).

The fumarate is prepared in the usual manner starting with 1.16 g of the above base in ethanol to give 1.21 g of compound of formula 25:

(25)

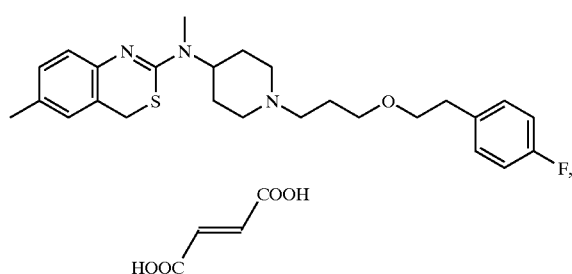

Empirical formula: $C_{30}H_{38}FN_3O_5S$; Molecular mass: 571.69; White crystals; Melting point: 169–172° C.; NMR (DMSO d$_6$) δ: 1.58–1.75 (m, 4H); 1.8–1.93 (m, 2H); 2.18–2.29 (m, 5H); 2.43–2.51 (m, 2H); 2.79 (t, 2H); 2.99 (s, 3H); 3–3.09 (m, 2H); 3.41 (t, 2H); 3.55 (t, 2H); 3.9 (s, 2H); 4.34 (m, 1H); 6.58 (s, 2H); 6.8 (d, 1H); 6.93–7 (m, 2H); 7.1 (t, 2H); 7.25–7.3 (m, 2H); 12–14 (m, 2H).

EXAMPLE 26

6-Chloro-N-methyl-N-[1-[3-[2-(4-fluorophenyl) ethoxy]-propyl]-4-piperidyl]-4H-3,1-benzothiazin-2-amine Hydrogen Fumarate (26)

26.1) 1-[1-[3-[2-(4-Fluorophenyl)ethoxy]propyl]-4-piperidyl]-1-methyl-3-[4-chloro-2-hydroxymethyl]-phenyl) thiourea (26.1). Working as described in Example 25.4, but starting with 880 mg (3 mmol) of diamine 25.3, the solution of thiocarbamoyl chloride 25.4.1 is prepared and is added to a solution of 470 mg (3.7 mmol) of 2-amino-5-chlorobenzyl alcohol. The hydroxy thiourea is, in this case, purified by flash chromatography to give a slightly colored oil (m=1.1 g; yield: 74%) of formula 26.1:

(26-1)

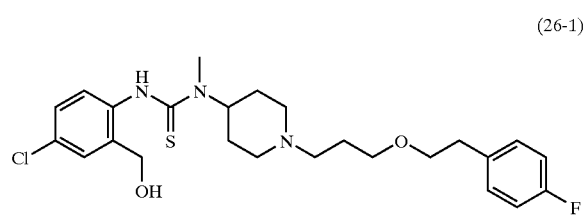

Empirical formula: $C_{25}H_{33}ClFN_3O_2S$; Molecular mass: 494.05; Amber-colored oil; NMR (CDCl$_3$) δ: 1.5–1.9 (m, 6H).; 2.02–2.15 (m, 2H); 2.39; (t, 2H); 2.84 (t, 2H); 2.92–3 (m, 2H); 3.11 (s, 3H); 3.44 (t, 2H); 3.6 (t, 2H); 4.59 (s, 2H); 5.18 (m, 1H); 6.95–7 (m, 2H); 7.13–7.22 (m, 2H); 7.23–7.33 (m, 2H); 7.72 (d, 1H); 7.98 (s, 1H).

26.2) 6-Chloro-N-methyl-N-[1-[3-[2-(4-fluorophenyl)-ethoxy]propyl]-4-piperidyl]-4H-3,1-benzothiazin-2-amine hydrogen fumarate (26). The cyclization-of 750 mg (1.52 mmol) of the above base 26.1 in 4 ml of concentrated hydrochloric acid according to the protocol of Example 25.5 gives 690 mg (yield: 96%) of powder of formula 26.2:

(26-2)

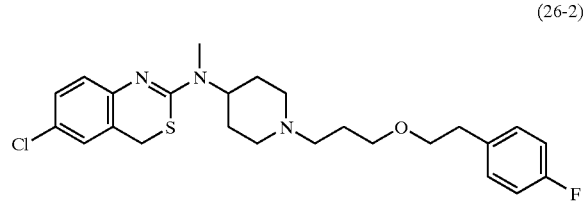

Empirical formula: $C_{25}H_{31}ClFN_3OS$; Molecular mass: 476.04; White crystals; Melting point: 72° C.; NMR (CDCl$_3$) δ: 1.63–1.92 (m, 6H); 2–2.09 (m, 2H); 2.32–2.44 (m, 2H); 2.8–2.87 (m, 2H); 2.93–3.02 (m, 2H); 3.09; (s, 3H); 3.47 (t, 2H); 3.55–3.63 (m, 2H); 3.81 (s, 2H); 4.38 (m, 1H); 6.92–7 (m, 3H); 7.05 (d, 1H); 7.12–7.2 (m, 3H).

The above base, salified in the usual manner, gives 695 mg of crystals (overall yield: 78%) of formula 26:

(26)

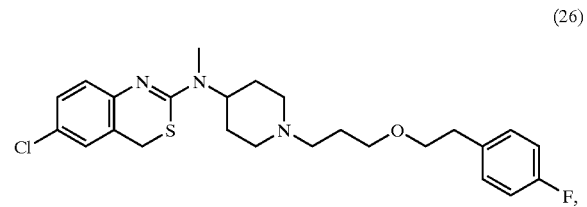

-continued

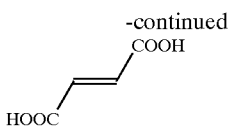

Empirical formula: $C_{29}H_{35}ClFN_3O_5S$; Molecular mass: 592.11; White crystals; Melting point: 167–170° C.; NMR (DMSO $d_6$) δ: 1.6–1.72 (m, 4H); 1.6–1.72 (m, 2H); 2.15 (t, 2H); 2.42 (t, 2H); 2.79 (t, 2H); 2.95–3.05 (m, 5H); 3.41 (t, 2H); 3.55 (t, 2H); 3.96 (s, 2H); 4.33 (m, 1H); 6.58 (s, 2H); 6.90 (d, 1H); 7.10 (t, 2H); 7.15–7.31 (m, 4H); 13 (m, 2H).

EXAMPLE 27

N-Methyl-N-[1-[3-[2-(4-fluorophenyl)ethoxy]propyl]-4-piperidyl]-6,7,8-trimethoxy-4H-3,1-benzothiazin-2-amine Hydrogen Fumarate (27)

27.1) 2-Amino-3,4,5-trimethoxybenzyl alcohol (27.1). By reduction of -12.06 g (50 mmol) of methyl 3,4,5-trimethoxyanthranilate according to the protocol of Example 25.1, the compound of formula 27.1 is prepared in a yield of 82%:

(27-1)

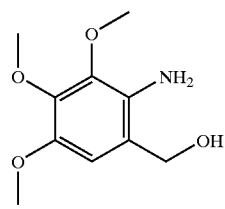

Empirical formula: $C_{10}H_{15}NO_4$; Molecular mass: 213.23; Beige-colored crystals; Melting point: 56–58° C.;

27.2) 1-[1-[3-[2-(4-Fluorophenyl)ethoxy]propyl]-4-piperidyl]-1-methyl-3-(6-hydroxymethyl-2,3,4-trimethoxyphenyl)thiourea (27.2). Starting with 880 mg (3 mmol) of diamine 25.3, the intermediate thio-carbamoyl chloride is prepared as described in Example 25.4, and is condensed with 640 mg (3 mmol) of 2-amino-3,4,5-trimethoxybenzyl alcohol 27.1 to give, after purification by flash chromatography, 1.22 g (yield: 73%) of an oil of formula 27.2:

(27-2)

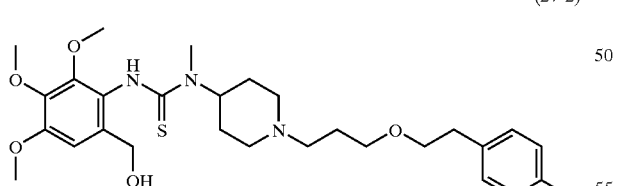

Empirical formula: $C_{28}H_{40}FN_3O_5S$; Molecular mass: 549.69; Amber-colored viscous oil; NMR (CDCl$_3$) δ: 1.65–1.85 (m, 6H); 2.06–2.16 (m, 2H); 2.35–2.45 (m, 2H); 2.84 (t, 2H); 2.95–3.03 (m, 2H); 3.19 (s, 3H); 3.46 (t, 2H); 3.6 (t, 2H); 3.84–3.92 (m, 11H); 4.51 (m, 1H); 5.19 (m, 1H); 6.63 (s, 1H); 6.84 (s, 1H); 6.92–7 (m, 2H) 7.14–7.21 (m, 2H).

27.3) N-Methyl-N-[1-[3-[2-(4-fluorophenyl)ethoxy]propyl]-4-piperidyl]-6,7,8-trimethoxy-4H-3,1-benzothiazin-2-amine hydrogen fumarate (27). By performing the cyclization of 950 mg (2.73 mmol) of the above hydroxy thiourea 27.2, according to the process described in Example 25.5, 698 mg (yield: 62%) of white powder of formula 27 are prepared:

(27)

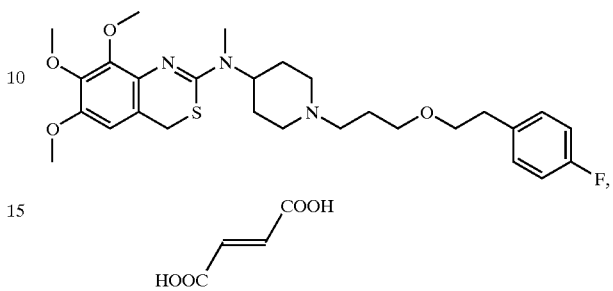

Empirical formula: $C_{32}H_{42}FN_3O_8S$; Molecular mass: 677.74; Pulverulent beige-colored crystals; Melting point: 68° C.; NMR (DMSO $d_6$) δ: 1.62–1.73 (m, 4H); 1.8–1.92 (m, 2H); 2.19 (t, 2H); 2.46 (t, 2H); 2.79 (t, 2H); 3.01 (s, 3H); 3–3.08 (m, 2H); 3.41 (t, 2H); 3.55 (t, 2H); 3.69 (s, 3H); 3.74 (s, 3H); 3.83; (s, 3H); 3.87 (s, 2H); 4.39 (m, 1H); 6.58 (s, 2H); 6.62 (s, 1H); 7.1 (t, 2H); 7.27 (t, 2H); 12–14 (m, 2H).

EXAMPLE 28

N-[1-[3-[2-(3,4-Difluorophenyl)ethoxy]propyl]-4-piperidyl]-4H-3,1-benzothiazin-2-amine Dihydrogen Fumarate (28)

By condensation of 910 mg (3.23 mmol) of 1-[2-(3-bromo-propoxy) ethyl]-3,4-difluorobenzene (prepared in Example 14.1) with 800 mg (3.23 mmol) of N-(4-piperidyl)-4H-3,1-benzothiazin-2-amine (prepared as described in patent application WO 97-05134) in the presence of 385 mg (3.56 mmol) of 98/02 $K_2CO_3$/KI in 8 ml of DMF according to the protocol of Example 1.2, and after addition of 2 equivalents of maleic acid, 985 mg (yield: 45%) of powder of formula 28 are prepared:

(28)

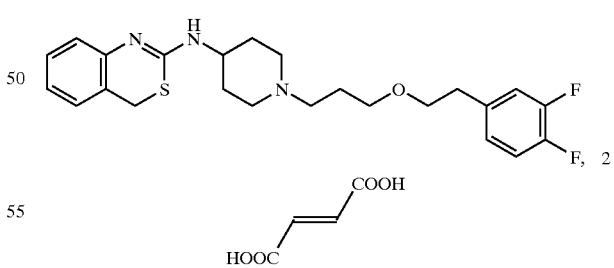

Empirical formula: $C_{32}H_{37}F_2N_3O_9S$; Molecular mass: 677.70; Pulverulent beige-colored crystals; Melting point: 166–168° C.; NMR (DMSO $d_6$) δ: 1.52–1.67 (m, 2H); 1.69–1.80 (m, 2H); 1.91–2.01 (m, 2H); 2.42–2.53 (m, 2H); 2.62 (t, 2H); 2.8; (t, 2H); 3.02–3.13 (m, 2H); 3.42 (t, 2H); 3.55 (t, 2H); 3.91 (s, 2H); 4.03 (m, 1H); 6.58 (m, 4H); 6.85–6.97 (m, 2H); 7.03–7.2 (m, 2H); 7.27–7.38 (m, 2H); 7.1–7.8 (m, 1H); 11.5–13.5 (m, 4H).

EXAMPLE 29

N-[1-[3-[2-(4-Fluorophenyl)ethoxy]propyl]-4-piperidyl]-4H-3,1-benzothiazin-2-amine Dihydrogen Fumarate (29)

Working as described in the above example, the compound of formula 29 is prepared in a yield of 42%:

(29)

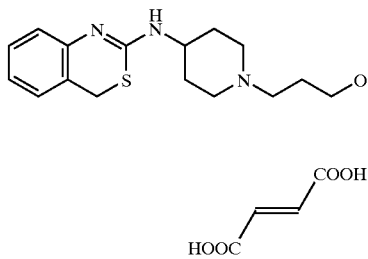

Empirical formula: $C_{32}H_{38}F_2N_3O_9S$; Molecular mass: 678.70; Pale cream-colored crystals; Melting point: 162–163° C.; NMR (DMSO $d_6$) δ: 1.52–1.66 (m, 2H); 1.68–1.83 (m, 2H); 1.94–2.01 (m, 2H); 2.4–2.52 (m, 2H); 2.61 (t, 2H); 2.79; (t, 2H); 3.03–3.1 (m, 2H); 3.41 (t, 2H); 3.55 (t, 2H); 3.9 (s, 2H); 4.03 (m, 1H); 6.58 (s, 4H); 6.87–6.97 (m, 2H); 7.05–7.19 (m, 4H); 7.24–7.3 (m, 2H); 7–7.6 (m, 1H); 11.8–13 (m, 4H).

EXAMPLE 30

N-[1-[3-[2-(4-Fluorophenyl)ethoxypropyl]-4-piperidyl]-4H-3,1-benzoxazin-2-amine Dihydrochloride Hydrate (30)

30.1) 1-[1-[3-[2-(4-Fluorophenyl)ethoxy]propyl]-4-piperidyl]-3-(2-hydroxymethylphenyl)urea (30.1). A solution of 0.77 g (2.58 mmol) of triphosgene in 50 ml of dry $CH_2Cl_2$ is cooled to 0° C. and then treated dropwise with a solution of 2.01 g (7.17 mmol) of 4-amino-1-[3-[2-(4-fluorophenyl)ethoxy]propyl]piperidine (prepared in a yield of 52% as described in Example 25.3 but using ammonium acetate as aminating agent) and 1.1 ml (7.88 mmol) of triethylamine in 20 ml of dry $CH_2Cl_2$. The reaction mixture is stirred overnight at 25° C. and is then treated dropwise with a solution of 885 mg (7.17 mmol) of ortho-aminobenzyl alcohol and 1 ml of triethylamine in 25 ml of dry $CH_2Cl_2$. Stirring is continued for 7 h at 25° C. and the reaction mixture is then washed with water and with brine, dried over anhydrous sodium sulfate and evaporated to dryness. The residual brown oil is slurried in isopropyl ether to give 2.16 g (yield: 70%) of compound of formula 30.1:

(30-1)

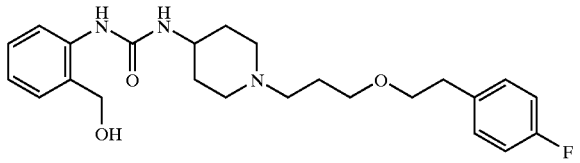

Empirical formula: $C_{24}H_{32}FN_3O_3$; Molecular mass: 429.52; Dark beige-colored powder; NMR ($CDCl_3$) δ: 1.35–1.47 (m, 2H); 1.65–1.78 (m, 2H); 1.86–1.99 (m, 2H); 2.05 (t, 2H); 2.34 (t, 2H); 2.72–2.88 (m, 4H); 3.44 (t, 2H); 3.55–3.74 (m, 3H); 4.66 (s, 2H); 5.08 (m, 1H); 6.96 (t, 2H); 7.02 (t, 1H); 7.11–7.21 (m, 3H); 7.23–7.3 (m, 2H); 7.57 (s, 1H); 7.79 (d, 1H).

30.2) N-[1-[3-[2-(4-Fluorophenyl)ethoxy]propyl]-4-piperidyl] -4H-3,1 -benzoxazin-2-amine dihydrochloride hydrate (30). Working as described in Example 25.5, but starting with 1.75 g (4.07 mmol) of the above hydroxy urea (30.1), the compound of formula 30 is prepared in a yield of 61%:

(30)

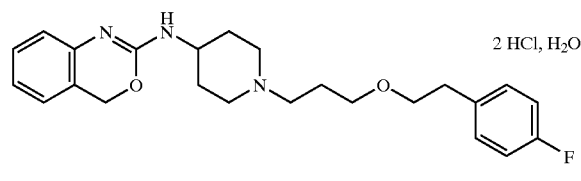

Empirical formula: $C_{24}H_{34}Cl_2FN_3O_3$; Molecular mass: 502.49; Pulverulent white crystals; Melting point: 158–159° C.; NMR ($CD_3OD$) 67 : 1.87–2.4 (m, 6H); 2.86 (t, 2H); 2.95–3.4; (m, 4H); 3.57 (t, 2H); 3.67 (t, 4H); 4.14 (m, 1H); 7.01; (t, 2H); 7.12–7.35 (m, 5H); 7.39–7.45 (m, 1H).

BIOLOGICAL EXPERIMENTS

The compounds of the present invention of formula I and the therapeutically acceptable salts thereof have advantageous pharmacological properties. These derivatives are active in vitro, on cardiomyocytes, by inhibiting the diastolic contracture induced with veratrine, on rat isolated left atrium. They also abolish the diastolic contracture induced by the global ischemia of infused isolated guinea pig heart according to the Langendorff technique. These compounds are also active in vivo, in reinfusion ischemia in anesthetized rabbits: they inhibit the electrical disturbances in the ECG which are caused by reinfusion ischemia, without any appreciable hemodynamic effect, and are not cardiac depressants. Such compounds are useful preventively or curatively in the treatment of coronaropathies, cardiac and cerebral ischemia in all their forms and in the treatment of atherosclerosis, cardiac insufficiency, pain, migraine and epilepsy.

1) Pharmacological Study

The experiments to which the chemical molecules which are the subject of the present invention were subjected demonstrated advantageous activity on the cardiovascular system both in"in vitro" and"in vivo" tests.

a)"In Vitro" Action

1) Inhibition of the contracture with veratrine, of rat isolated left atrium, was carried out according to the technique of Le Grand et al. (Naunyn—Schmiedeberg's Arch Pharmacol (1993) 348 p 184–190). The results are given in Table I. The percentages of inhibition are relative to a concentration of $10^{-7}$ M of test compound.

TABLE I

| Compound No. | Ex. 5 | Ex. 6 | Ex. 14 | Ex. 23 | R56865* | Sabeluzole** | Control*** |
|---|---|---|---|---|---|---|---|
| % inhibition at $10^{-7}$ M | 63% | 41% | 32% | 35% | 32% | 5% | 26% |

*N-(1-(4-(4-fluorophenoxy)butyl)4-piperidyl)-N-methyl-2-benzothiazolamine.
**N-(1-(2-hydroxy-3-(4-fluorophenoxy)propyl-4-piperidyl)-N-methyl-2-benzothiazolamine mentioned in patent EP 0 184 257 and in development.
***N-Methyl-N-[1-[4-(3,4-difluorophenoxy)butyl]-4-piperidyl]-4H-3,1-benzothiazin-2-amine (WO 97/05134 from the Applicant).

2) Inhibition of the diastolic contracture induced by the global ischemia of infused isolated guinea pig heart is carried out according to the technique described by Le Grand B. et al. (Am. J. Physiol. 269, H533-H540 (1995)). The guinea pig hearts collected are infused with a modified Krebs solution and, after stabilization for 20 minutes, the test compound dissolved in water or in aqueous 1% DMSO solution is added. After 15 minutes, global ischemia is induced by stopping the coronary infusion for 50 minutes, followed by reinfusion for 1 h. The inhibition of ischemic contracture, in the presence of the compounds of the present invention, is measured relative to that obtained in the vehicle group. The results are given in Table II by way of non-limiting example at a concentration of 1 μM.

TABLE II

| Compounds | of Example 6 | of Example 14 | Control*** F | HOE 694**** |
|---|---|---|---|---|
| % diastolic contracture inhibition at 1 μM | 79% | 77% | 48% | 17% |

***see Table I
****3-(Methylsulfonyl-4-piperidinobenzoyl)guanidine hydrochloride (EP 418 499).

b)"In Vivo," Activity

The compounds of the present invention are also active via the oral route in the test of ischemia-reinfusion in anesthetized rabbits, according to the method of Verscheure et al. (*J. Cardiovasc Pharmacol* (1995) 25 p 126–133). The results for the compounds of Examples 6 and 14 are given in Table III below, by way of non-limiting example:

TABLE III

| Compound No. | Dose mg/kg p.o. | % inhibition of over-increase of ST segment | Number of animals with reinfusion arrhythmia | % change in heart rate | % change in arterial pressure |
|---|---|---|---|---|---|
| 6 | 0.63 | 42% | 3/5 | -7 | 0 |
| 14 | 0.63 | 83% | 0/5 | -5 | 3 |
| R 56865* | 10 | 100% | 0/5 | 5 | 15 |
| R 56865* | 2.5 | 0% | 2/5 | 0 | 27 |
| Sabeluzole** | 10 | 34% | 3/4 | 0 | 12 |
| Control*** F | 0.63 | 31% | 1/5 | 0 | 5 |

*, , *: see Table I

2) Therapeutic Applications

The compounds of the present invention and the therapeutically acceptable salts thereof are useful as medicinal products. These compounds are more particularly suitable in cardiology in the prophylactic treatment of cardiovascular diseases such as:

myocardial ischemia and coronaropathies and more particularly in attacks:
of chronic stable angina,
unstable angina and Prinzmetal's angina,
silent ischemia, and in the prevention of reocclusions, restenoses and reinfarction,
cerebral ischemia and more specifically in:
cerebrovascular accidents,
transient ischemic attacks,
neurodegenerative diseases,
atherosclerosis,
cardiac insufficiency,
hypertension.

These compounds may also be used in the treatment of epilepsy, migraine and pain. These compounds may be administered orally, parenterally or rectally. Each dose consists of an inert adjuvant promoting the preparation and absorption of the medicinal product; the active principle may also be combined with another.

These medicinal products may be in solid form (tablets or gel capsules) or liquid form to be made up at the time of use (suspensions, emulsions, syrups, solutions or the like) or suppositories. The active principle is administered at an average dose of between 0.1 and 10 mg/kg of bodyweight. Two preparations are given as nonlimiting examples. The ingredients and also other therapeutically acceptable ingredients may be introduced in other proportions without modifying the scope of the invention.

EXAMPLE 31

Injectable solution to be made up at the time of use.

1) A sterile inactinic glass flask for injectable preparation containing:

N-Methyl-N-[1-[3-[2-(3,4-difluorophenyl)ethoxy]propyl]-4-piperidyl]-4H-3,1-benzothiazin-2-amine hydrogen maleate - - - 5 mg 2) A sterile glass ampoule of solvent containing:

Propylene glycol - - - 100 mg
Anhydrous dextrose - - - 50 mg
Sterile distilled water qs - - - 2 ml

EXAMPLE 32

Splittable tablets

N-Methyl-N-[1-[3-[2-(3,4-difluorophenyl)ethoxy]propyl]-4-piperidyl]-4H-3,1-benzothiazin-2-amine hydrogen maleate - - - 30 mg
Lactose hydrate - - - 80 mg Microcrystalline cellulose - - - 20 mg
Magnesium stearate - - - 4 mg
Corn starch - - - 16 mg
Talc - - - 4 mg
Polyvinylpyrrolidone - - - 6 mg
Total weight - - - 160 mg Splittable tablets to be stored away from heat and moisture.

What is claimed is:

1. A compound of formula I:

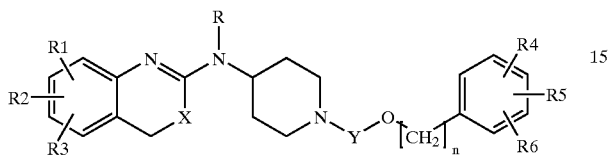

in which:
X represents an oxygen or sulfur atom,
Y represents either:
a branched or unbranched alkylene radical containing from consisting of 2 to 6 carbon atoms or
a —CH$_2$—CH(OH)—CH$_2$— radical
R represents: a hydrogen, a saturated or unsaturated, branched or unbranched alkyl radical consisting of 1 to 7 carbon atoms,
R$_1$ to R$_6$, which may be identical or different, represent:
a hydrogen,
a branched or unbranched, saturated or unsaturated alkyl consisting of 1 to 5 carbon atoms,
a branched or unbranched, saturated or unsaturated alkyloxy consisting of 1 to 5 carbon atoms,
a halo group,
a nitro group,
a hydroxyl group,
an acyl or acyloxy group consisting of 2 to 3 carbon atoms,
a dialkylamino group consisting of 1 to 5 carbon atoms,
a trifluoromethyl or trifluoromethoxy group,
n is an integer which may range from 1 to 6 inclusive, its pure enantiomers thereof or mixtures thereof, and the therapeutically acceptable mineral or organic salts of the compounds of formula I and the possible hydrates thereof.

2. The compound as claimed in claim 1, selected from the following compounds:
N-Methyl-N-[1-[5-(4-fluorobenzyloxy)pentyl]-4-piperidyl]-4H-3,1-benzothiazin-2-amine hydrogen fumarate,
N-Methyl-N-[1-[4-(4-fluorobenzyloxy)butyl]-4-piperidyl]-4H-3,1-benzothiazin-2-amine hydrogen fumarate,
N-Methyl-N-[1-[3-(4-fluorobenzyloxy)propyl]-4-piperidyl]-4H-3,1-benzothiazin-2-amine hydrogen fumarate,
N-Methyl-N-[1-[-2-(4-fluorobenzyloxy)ethyl]-4-piperidyl]-4H-3,1-benzothiazin-2-amine hydrogen fumarate,
N-Methyl-N-[1-[4-[2-(4-fluorophenyl)ethoxy]butyl]-4-piperidyl]-4H-3,1-benzothiazin-2-amine hydrogen fumarate,
N-Methyl-N-[1-[3-[2-(4-fluorophenyl)ethoxy]-4-propyl]-4-piperidyl]-4H-3,1-benzothiazin-2-amine hydrogen fumarate,
N-Methyl-N-[1-[3-[2-(4-fluorophenyl)ethoxy]-4-propyl]-4-piperidyl]-4H-3,1-benzothiazin-2-amine dihydrochloride,
N-Methyl-N-[1-[3-[3-(4-fluorophenyl)propoxy]propyl]-4-piperidyl]-4H-3,1-benzothiazin-2-amine hydrogen fumarate,
N-Methyl-N-[1-[2-[2-(4-fluorophenyl)ethoxy]ethyl]-4-piperidyl]4H-3,1-benzothiazin-2-amine hydrogen fumarate,
N-Methyl-N-[1-[5-(3,4-difluorophenylmethoxy)pentyl)-4-piperidyl]-4H-3,1-benzothiazin-2-amine hydrogen fumarate,
N-Methyl-N-[1-[4-[3,4-difluorophenylmethoxy)butyl]-4-piperidyl]-4H-3,1-benzothiazin-2-amine hydrogen fumarate,
N-Methyl-N-[1-[3-(3,4-difluorophenylmethoxy)propyl]4-piperidyl]-4H-3,1-benzothiazin-2-amine hydrogen fumarate,
N-Methyl-N-[1-[4-[2-(3,4-difluorophenyl)ethoxy]butyl]4-piperidyl]4H-3,1-benzothiazin-2-amine hydrogen fumarate,
N-Methyl-N-[1-[3-[2-(3,4-difluorophenyl)ethoxy]propyl]4-piperidyl]4H-3,1-benzothiazin-2-amine hydrogen fumarate,
N-Methyl-N-[1-[5-(4-methoxyphenylmethoxy)pentyl]4-piperidyl]-4H-3,1-benzothiazin-2-amine hydrogen fumarate,
N-Methyl-N-[1-[4-(4-methoxyphenylmethoxy)butyl]-4-piperidyl]-4H-3,1-benzothiazin-L-amine hydrogen fumarate,
N-Methyl-N-[1-[3-[4-methoxyphenylmethoxy)propyl]-4-piperidyl]-4H-3,1-benzothiazin-2-amine hydrogen fumarate,
N-Methyl-N-[1-[4-[2-(4-methoxyphenyl)ethoxy]butyl]-4-piperidyl]-4H-3,1-benzothiazin-2-amine hydrogen fumarate,
N-Methyl-N-[1-[3-[2-(4-methoxyphenyl)ethoxy]propyl]-4-piperidyl]-4H-3,1-benzothiazin-2-amine hydrogen fumarate,
N-Methyl-N-[1-[2-[2-(4-methoxyphenyl)ethoxy]ethyl]-4-piperidyl]-4H-3,1-benzothiazin-2-amine hydrogen fumarate,
N-Methyl-N-[1-(2-phenylmethoxyethyl)-4-piperidyl]-4H-3,1-benzothiazin-2-amine hydrogen fumarate,
N-Methyl-N-[1-[3-(2-phenylethoxy)propyl]-4-piperidyl]-4H-3,1-benzothiazin-2-amine hydrogen fumarate,
N-Methyl-N-[1-[2-hydroxy-3-(4-fluorophenylmethoxy)propyl]-4-piperidyl]-4H-3,1-benzothiazin-2-amine hemifumarate,
N-Methyl-N-[1-[2-hydroxy-3-[2-(4-methoxyphenyl)ethoxy]propyl]-4-piperidyl]-4H-3,1-benzothiazin-2-amine hydrogen fumarate,
6,N-Dimethyl-N-[1-[3-[2-(4-fluorophenyl)ethoxy]propyl]-4-piperidyl]-4H-3,1-benzothiazin-2-amine hydrogen fumarate,
6-Chloro-N-methyl-N-[1-[3-[2-(4-fluorophenyl)ethoxy]propyl]-4-piperidyl]-4H-3,1-benzothiazin-2-amine hydrogen fumarate,
N-Methyl-N-[1-[3-[2-(4-fluorophenyl)ethoxy]propyl]-4-piperidyl]-6,7,8-trimethoxy-4H-3,1-benzothiazin-2-amine hydrogen fumarate,
N-[1-[3-[2-(4-fluorophenyl)ethoxy]propyl]4-piperidyl]-4H-3,1-benzothiazin-2-amine dihydrogen fumarate, N-[1-[3-[2-(4-fluorophenyl)ethoxy]propyl]-4-piperidyl]-4H-3,1-benzothiazin-2-amine dihydrogen fumarate, N-[1-[3-[2-(4-fluorophenyl)ethoxy]propyl]-4-piperidyl]-4H-3,1-benzoxazin-2-amine dihydrochloride hydrate, N-Methyl-N-[1-[3-[2-(4-fluorophenyl)ethoxy]propyl]-4-piperidyl]-4H-3,1-benzothiazin-2-amine, N-Methyl-N-[1-[3-[3-(4-fluorophenyl)propoxy]propyl]-4-piperidyl]4H-3,1-benzothiazin-2-amine, N-Methyl-N-[1-[3-[2-(3,4-difluorophenyl)ethoxy]propyl]-4-piperidyl]-4H-3,1-benzothiazin-2-amine, N-Methyl-N-[1-[3-(2-phenylethoxy)propyl]-4-piperidyl]-4H-3,1-benzothiazin-2-amine, 6,N-Dimethyl-N-[1-[3-[2-(4-fluorophenyl)ethoxy]propyl]-4-piperidyl]-4H-3,1-benzothiazin-2-amine, 6-Chloro-N-methyl-N-[1-[3-[2-(4-fluorophenyl)ethoxy]propyl]-4-piperidyl]-4H-3,1-benzothiazin-2-amine, and N-Methyl-N-[1-[3-[2-(4-fluorophenyl)ethoxy]propyl]4-piperidyl]-6,7,8-trimethoxy-4H-3,1-benzothiazin-2-amine.

3. A process for preparing a chemical compound of claim 1, wherein the intermediate amine (X):

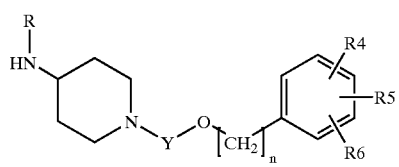

(X)

is activated in the form of the carbamoyl chloride or thiocarbamoyl chloride of formula XIV:

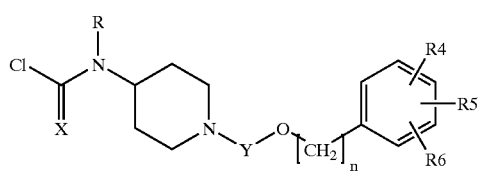

(XIV)

this intermediate, which is not isolated, may be prepared by reacting (thio)phosgene with the amine X in the presence of a base, in an aprotic halogenated solvent ($CH_2Cl_2$ or $C_2H_4Cl_2$) or an ether, the intermediate then being condensed with an o-aminobenzyl alcohol of formula XII:

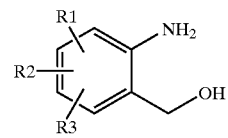

(XII)

in the above solvent at a temperature of between 10° C. and 40° C. to give the intermediate hydroxymethyl(thio)urea XV, which is generally recovered by recrystallization:

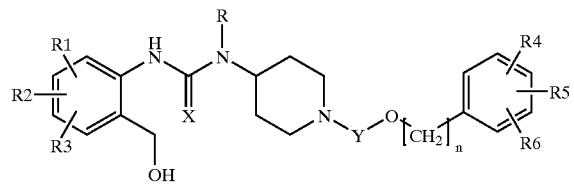

(XV)

this product (XV) is readily cyclized in a concentrated aqueous hydracid solution at a temperature between 20 and 80° C., to give the compound of general formula (I), wherein, in formulae X, XII, XIV and XV, the radicals R, $R_1$ to $R_6$, n, X and Y have the same meaning as in claim 1.

4. A pharmaceutical composition, characterized in that it contains as active principle at least one compound as claimed in claim 1, combined with an inert pharmaceutical support, or other pharmaceutically acceptable vehicles, which may or may not be combined with another medicinal product.

5. A method of treating a living body afflicted with a condition requiring the treatment of myocardial ischemia, chronic stable angina, unstable angina and prinzmetal's angina attacks, silent cardiac ischemia, reinfarction, reocclusion and restenosis, comprising the step of administering a compound of claim 1 which is effective for alleviation of the condition.

6. A method of treating a living body afflicted with a condition selected from cerebral ischemia, cerebrovascular accidents, and transient ischemic attacks comprising the step of administering a compound of claim 1 which is effective for alleviation of the condition.

7. A method of treating a living body afflicted with a condition selected from cardiac insufficiency and hypertension, comprising the step of administering a compound of claim 1 which is effective for alleviation of the condition.

8. A method or treating a living body afflicted with a condition selected from epilepsy, migrain and pain, comprising the step of administering a compound of claim 1 which is effective for alleviation of the condition.

* * * * *

UNITED STATES PATENT AND TRADEMARK OFFICE
CERTIFICATE OF CORRECTION

PATENT NO.     : 6,531,469 B1
DATED          : March 11, 2002
INVENTOR(S)    : Jean-Pierre Rieu et al.

It is certified that error appears in the above-identified patent and that said Letters Patent is hereby corrected as shown below:

<u>Title page,</u>
Item [56], OTHER PUBLICATIONS, "Damasio reference", "1992-1996" should be -- 1992-6, 1996 --; and "Layzer reference", remove second 1996.

<u>Column 37,</u>
Lines 24/25, remove "containing from"
Line 65, "ethoxy]-4-propyl]" should be -- ethoxy]propyl] --.

<u>Column 38,</u>
Line 1, "ethoxy]-4-propyl]" should be -- ethoxy]propyl] --.

Signed and Sealed this

Seventeenth Day of June, 2003

JAMES E. ROGAN
*Director of the United States Patent and Trademark Office*